US009101635B2

(12) United States Patent
Basu et al.

(10) Patent No.: US 9,101,635 B2
(45) Date of Patent: Aug. 11, 2015

(54) INHIBITORS OF FILOVIRUS ENTRY INTO HOST CELLS

(75) Inventors: Arnab Basu, Newton Lower Falls, MA (US); Debra M. Mills, Ayer, MA (US); Norton P. Peet, North Andover, MA (US); John D. Williams, Worcester, MA (US)

(73) Assignee: MICROBIOTIX, INC., Worcester, MA (US)

( * ) Notice: Subject to any disclaimer, the term of this patent is extended or adjusted under 35 U.S.C. 154(b) by 546 days.

(21) Appl. No.: 13/383,345

(22) PCT Filed: Jul. 10, 2010

(86) PCT No.: PCT/US2010/041632
§ 371 (c)(1), (2), (4) Date: Jan. 10, 2012

(87) PCT Pub. No.: WO2011/046646
PCT Pub. Date: Apr. 21, 2011

(65) Prior Publication Data

US 2012/0189614 A1 Jul. 26, 2012

Related U.S. Application Data

(60) Provisional application No. 61/270,606, filed on Jul. 10, 2009.

(51) Int. Cl.

| | |
|---|---|
| ***A61K 31/18*** | (2006.01) |
| ***A61K 31/5513*** | (2006.01) |
| ***C07D 213/74*** | (2006.01) |

(Continued)

(52) U.S. Cl.
CPC ............ *A61K 31/5513* (2013.01); *A61K 31/18* (2013.01); *C07D 213/74* (2013.01); *C07D 215/40* (2013.01); *C07D 243/12* (2013.01); *C07D 249/10* (2013.01); *C07D 307/71* (2013.01); *C07D 405/06* (2013.01); *C07D 405/12* (2013.01); *C07D 405/14* (2013.01);
(Continued)

(58) Field of Classification Search
CPC ....................................................... A61K 31/18
USPC ........................................................... 514/604
See application file for complete search history.

(56) References Cited

U.S. PATENT DOCUMENTS

2002/0128262 A1 9/2002 Hurst et al.
2004/0229817 A1 11/2004 Duggal et al.

(Continued)

OTHER PUBLICATIONS

Noueiry et al. "Identification of Novel small-molecule inhibiitors of West Nile virus infection," J. Voirol. 2007, vol. 81, No. 21, pp. 11992-12004.*

(Continued)

*Primary Examiner* — Shengjun Wang
(74) *Attorney, Agent, or Firm* — Yankwich & Associates, P.C.; Leon R. Yankwich; Michael R. Wesolowski

(57) ABSTRACT

Organic compounds showing the ability to inhibit viral glycoprotein (GP)-mediated entry of a filovirus into a host cell are disclosed. The disclosed filovirus entry inhibitor compounds are useful for treating, preventing, or reducing the spread of infections by filovirus including the type species Marburg virus (MARV) and Ebola virus (EBOV). Preferred inhibitors of the invention provide therapeutic agents for combating the Ivory Coast, Sudan, Zaire, Bundibugyo, and Reston Ebola virus strains.

6 Claims, 9 Drawing Sheets

(51) Int. Cl.

| | |
|---|---|
| ***C07D 215/40*** | (2006.01) |
| ***C07D 243/12*** | (2006.01) |
| ***C07D 249/10*** | (2006.01) |
| ***C07D 307/71*** | (2006.01) |
| ***C07D 405/06*** | (2006.01) |
| ***C07D 405/12*** | (2006.01) |
| ***C07D 405/14*** | (2006.01) |
| ***C07D 409/04*** | (2006.01) |
| ***C07D 471/04*** | (2006.01) |
| ***C07D 491/22*** | (2006.01) |

(52) U.S. Cl.
CPC ............ *C07D 409/04* (2013.01); *C07D 471/04* (2013.01); *C07D 491/22* (2013.01)

(56) References Cited

U.S. PATENT DOCUMENTS

| | | | | |
|---|---|---|---|---|
| 2005/0266022 | A1 | 12/2005 | Goldsmith et al. | |
| 2008/0124303 | A1 | 5/2008 | King | |
| 2008/0249131 | A1 | 10/2008 | Girardet et al. | |
| 2011/0165220 | A1 * | 7/2011 | Lambert et al. ............... | 424/431 |

OTHER PUBLICATIONS

International Search Report for international application No. PCT/US2010/41632 (Nov. 8, 2011).
Written Opinion of the International Searching Authority for international application No. PCT/US2010/41632 (Nov. 8, 2011).

* cited by examiner

```
┌─────────────────────────────────────────────────────────────┐
│ HTS of 100,500 discrete compounds and natural products at   │
│    25μM concentration using HIV/EBOV-GP in 293T cells       │
└─────────────────────────────────────────────────────────────┘
        <90% inhibition    │    >90% inhibition
              ↓            │           ↓
    ┌──────────────────┐   │   ┌──────────────┐
    │No further interest│  │   │ Primary Hits │
    └──────────────────┘   │   └──────────────┘
         ↑ ↑ ↑ ↑                      ↓
         │ │ │ │         ┌────────────────────────────────┐
         │ │ │ │ >50% inhibition │ Counter screen against HIV/VSV-G │
         │ │ │ └─────────│ for identification of specific HIV/EBOV-GP │
         │ │ │           │         inhibitors at 25μM           │
         │ │ │           └────────────────────────────────┘
         │ │ │                     │ <50% inhibition
         │ │ │   CC50<25μM         ↓
         │ │ └──────────  ┌────────────────────────────────┐
         │ │              │ Screened for cytotoxicity in 293T cells │
         │ │              └────────────────────────────────┘
         │ │                       │ CC50>25μM
         │ │                       ↓
         │ │   Not Confirmed  ┌────────────────────────────────┐
         │ └──────────────────│ Hits were reordered from different │
         │                    │   batches from original vendors,    │
         │                    │            reconfirmed              │
         │                    └────────────────────────────────┘
         │                              ↓
         │   Not Confirmed   ┌────────────────────────────────┐
         └───────────────────│ Confirmed against infectious EBOV │
                             │        virus (IC50<20 μM)           │
                             └────────────────────────────────┘
                                       ↓
                             ┌────────────────────┐
                             │ Anti-EBOV inhibitors│
                             └────────────────────┘
```

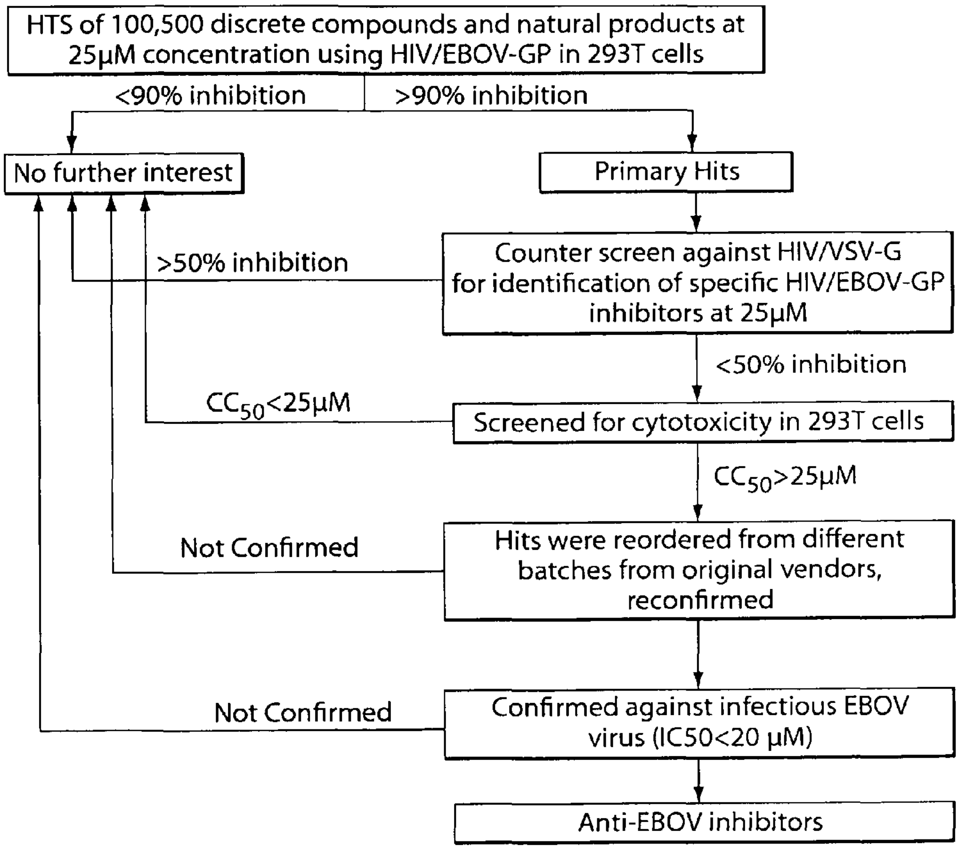

Fig. 4

INHIBITORS OF FILOVIRUS ENTRY INTO HOST CELLS

CROSS-REFERENCE TO PRIORITY APPLICATIONS

This application is a United States national stage filing under 35 U.S.C. §371of international (PCT) application no. PCT/US2010/041632, filed Jul. 10, 2010, and designating the U.S, which claims priority to U.S Provisional Appln. No. 61/270,606filed Jul. 10, 2009.

STATEMENT REGARDING FEDERALLY SPONSORED RESEARCH

This invention was made with government support under grant AI071450 awarded by the National Institutes of Health. The government has certain rights in the invention.

FIELD OF THE INVENTION

This invention is in the field of therapeutic drugs to treat viral infection and disease. In particular, the invention provides organic compounds that inhibit entry of one or more filoviruses into host cells.

BACKGROUND OF THE INVENTION

Filoviruses are enveloped, nonsegmented, negative-stranded (NNS) RNA viruses and constitute a distinct family within the order Mononegavirales. The family includes Marburg viruses, causing Marburg disease (green monkey disease), and Ebola virus (EBOV), causing hemorrhagic fever. The Ebola viruses are further subdivided into four distinct African (Ivory Coast, Sudan, Zaire, and Bundibugyo) and a single Asian (Reston) species. EBOV Zaire (EboZ) and Sudan (EboS) are highly pathogenic in human and nonhuman primates, with a mortality rate up to 80-90%. Peters, C. J., et al., *Curr. Top. Microbiol. Immunol.,* 235:85-95 (1999); Sanchez, A., et al. *Filoviridae: Marburg and Ebola viruses*, p. 1279-1304, D. M. Knipe and P. M. Howley (ed.), *Fields virology*, Lippincott, Williams & Wilkins, Philadelphia, Pa. (2001). In contrast, EBOV Ivory Coast (EboC), EBOV Bundibugyo, and EBOV Reston (EboR) are less virulent, with EboR infecting only non-human primates (Sanchez, A., et al., (2001) op. cit.). EBOV infections are pantropic, but no single organ shows sufficient damage to account for the onset of severe shock and bleeding. As with other viral hemorrhagic fevers, EBOV infections are associated with fluid distribution problems, hypotension, coagulation disorders and bleeding, finally resulting in fulminate shock.

Ebola virus is classified as a biosafety level-4 (BSL-4) agent because of its high mortality rate and the lack of approved vaccines and antivirals to prevent or treat it (Peters, C. J., et al., op. cit.; Sanchez, A., et al. (2001), op. cit.). EBOV has also been classified as a Category A bioweapons agent by the Centers for Disease Control and Prevention (CDC) because of its high virulence, demonstrated aerosol infectivity in the laboratory, and capacity for inducing fear and anxiety. See, Bossi, P., et al., *Cell Mol. Life. Sci.,* 63:2196-212 (2006).

Several promising vaccine candidates have been shown to be effective in eliciting host immune responses and protecting primates against EBOV infection. Sullivan, N., et al., *Nature,* 424:681-684 (2000); Sullivan N., et al., *J. Virol.,* 77:9733-9737 (2003). Nonetheless, the minimal time required for protective vaccination (more than one month), the sporadic nature of filoviral outbreaks and the potential for bioterrorism, underscore the urgent need to develop potent inhibitors for EBOV infection. Bray, M., *Antiviral Res.,* 57:53-60 (2003).

There are currently no approved therapeutic interventions for EBOV infections. A limited number of small-molecule research inhibitors of EBOV infections have been reported to date. Bray M., et al., *Antiviral Res.,* 54:1-17 (2002); Hensley, L. E., et al., *Curr. Mol. Med.,* 5:761-72 (2005); Stroher, U., et al., *Expert Opin. Investig. Drugs.,* 15:1523-35 (2006). These low molecular weight anti-EBOV agents can be characterized by three general modes of action: a) impairment of viral mRNA methylation; b) stimulation of innate antiviral mechanisms; and c) prevention of virion entry and/or fusion.

The carbocyclic adenosine analog 3-deazaadenosinc (C-c3Ado) has been shown to inhibit cellular S-adenosylhomocysteine hydrolase and EboZ replication in vitro, with an $IC_{50}$ of 30 μM. Huggins, J., et al., *J. Infect. Dis.,* 179:S240-7 (1999). The activity of C-c3Ado has been attributed to diminished methylation of the 5' cap of viral mRNA by methyltransferase, which impairs the translation of viral transcripts. Administration of C-c3Ado to EBOV-infected mice has also been found to dramatically increase production of IFN-α and protects mice against EBOV infection. Huggins, J., et al., op. cit. However, C-c3Ado failed to induce IFN-α production and did not protect against EBOV infections in monkeys. Bray, M., et al., *Antiviral Res.,* 55:151-9 (2002).

The glycodendritic compound, BH30sucMan, which contains 32 individual α-mannose units linked to the hyperbranched dendrimer BH30 through succinyl spacers, has recently been shown to block C-type lectins dendritic cell-specific intercellular adhesion molecule 3-grabbing nonintegrin (DC-SIGN) mediated EBOV infection of Jurkat cells at high nanomolar concentrations ($IC_{50}$=337 nM) (Lasala, F., et al., *Antimicrob. Agents Chemother.,* 47:3970-2 (2003)).

EBOV enters target cells by an endocytic pathway. Therefore, compounds that disrupt the efficient internalization of the endosomal vesicles, via the various components of the cytoskeleton, or endosome acidification, can potentially abrogate EBOV entry and fusion into cells. Latrunculin and colchicine impair the formation of microfilaments and microtubules, respectively, and have been shown to inhibit the infection of EBOV GP pseudotypes (Yonezawa, A., et al., *J. Virol.,* 79:918-26 (2005)). Similarly, HeLa cells pretreated with the bafilomycin A1 (Lasala, F., et al., op. cit.), an inhibitor of vacuolar ATPase, are shown to be resistant to infection by pseudotyped HIV type 1 virions (Yonezawa, A., et al., op. cit.).

Recently, two groups have independently demonstrated that cathepsin B (CatB) and cathepsin L (CatL) mediate viral entry by carrying out proteolysis of the EBOV GP 1 subunit. Chandran, K., et al., *Science,* 308:1643-1645 (2005); Schornberg, K., et al., *J. Virol.,* 80:4174-8 (2006). Selective inhibitors of the CatB such as CA-074 or CA-074Me, were shown to greatly reduce the infectivity of EBOV pseudotypes. Unfortunately, given the demonstrated hypersensitivity of EBOV GP1 to digestion by other proteases, such as thermolysin, the clinical prospects for antiviral agents that solely target CatB and CatL is not encouraging. Jane-Valbuena, J., et al., *J. Virol.,* 76:5184-97 (2002).

Interfering with the viral entry process is an attractive strategy for controlling viral infection. Entry of EBOV and other filoviruses into a host cell is mediated by a single viral glycoprotein (GP), a class I fusion protein. EBOV-GP consists of GP1 and GP2 subunits, which are linked by disulfide bonds and non-covalent interactions. GP1 is responsible for receptor binding and host tropism, while GP2 mediates viral/cell membrane fusion during viral entry.

Viral entry inhibitors can disrupt the viral life cycle and therefore prevent or treat infection. For example, enfuvirtide (marketed under the trade name Fuzeon® (also known as T-20) by Hoffmann-La Roche Ltd.) is a synthetic 36-amino-acid peptide that binds to a region of the envelope glycoprotein 41 of HIV type 1 (HIV-1) that is involved in the fusion of the virus with the membrane of CD4+ host cells. See, Wild, C., et al., *AIDS Res. Hum. Retroviruses,* 9:1051-3 (1993). However, T-20 has also highlighted the potential problems of peptidic antivirals that include lack of absorption from the gastrointestinal tract necessitating intravenous delivery and a high manufacturing cost.

Clearly, needs remain for new, potent inhibitors against EBOV and other filovirus infections. Inhibitors that could be used during natural outbreaks or bio-terrorist attacks, and that could be used either prophylactically to treat a potentially exposed population or therapeutically after exposure or infection, would be especially desirable.

SUMMARY OF THE INVENTION

The invention addresses the above needs by providing new filovirus entry inhibitor compounds of different chemotypes. To identify filovirus entry inhibitor compounds described herein, a HIV-based EBOV pseudotype virus (HIV/EBOV-GP), wherein EBOV GP was incorporated into lentiviral pseudotypes, was developed and employed as a high throughput screen (HTS) assay to identify putative entry inhibitors of EBOV and other filoviruses. Libraries of thousands of discrete small molecule organic compounds and purified natural products were screened using this assay. The EBOV-GP entry inhibitor compounds ("hits") from the high throughput primary screen were then qualified through a series of secondary assays, including a HIV-based vesicular stomatitis virus (VSV) pseudotype (HIV/VSV-G) virus, as a counter screen to eliminate non-specific inhibitors, and cytotoxicity testing. The qualified, confirmed hits were validated as active against infectious recombinant EBOV.

Accordingly, a filovirus entry inhibitor compound described herein inhibits viral glycoprotein (GP)-mediated entry of a filovirus into a host cell (e.g., human or other animal cell). Preferred filovirus entry inhibitor compounds described herein inhibit viral glycoprotein (GP)-mediated entry by inhibiting the binding of the virus with its receptor or inhibiting the fusion process.

In preferred embodiments, a filovirus GP-mediated entry inhibitor compound according to the present invention inhibits Marburg viruses and Ebola viruses.

In another embodiment, a filovirus GP-mediated entry inhibitor compound described herein inhibits one or more species of EBOV, and especially preferred embodiments will inhibit infection by EBOV Sudan and/or Zaire species.

The present invention provides isolated filovirus entry inhibitor compounds of the formulae:

A.

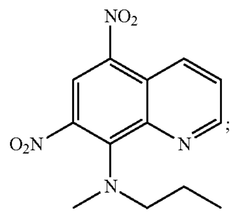

B.

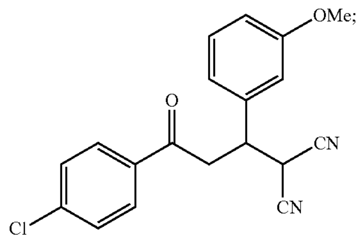

C.

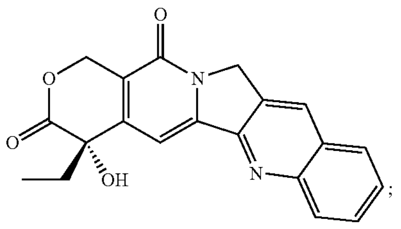

D.

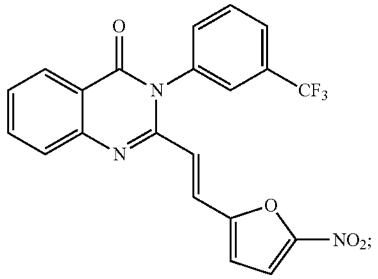

E.

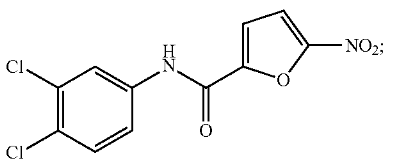

F.

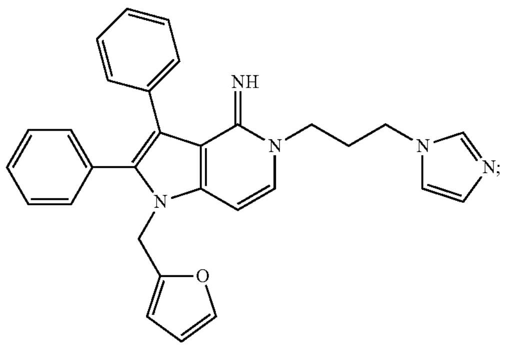

-continued

G.

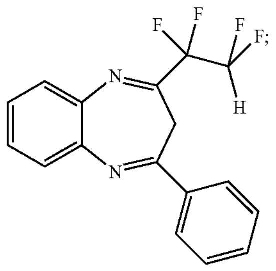

H.

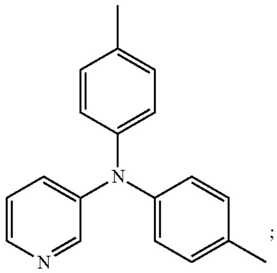

;

I.

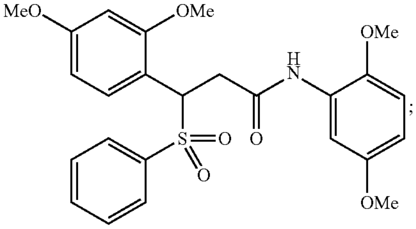

J.

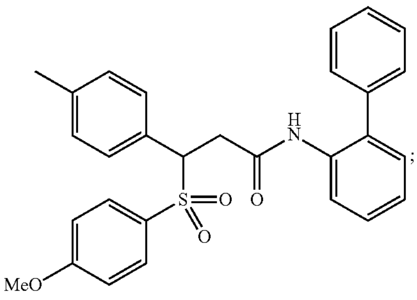

; and

K.

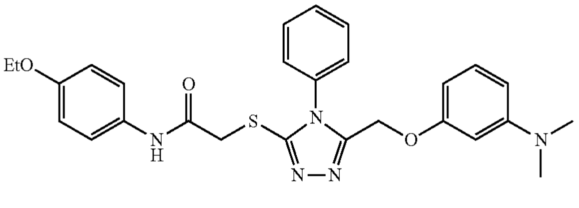

The present invention further provides isolated filovirus entry inhibitor compounds of the formula:

G-1

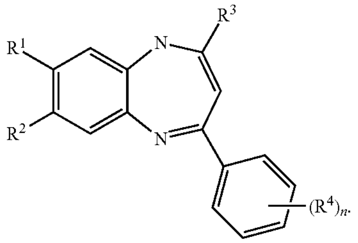

wherein $R^1$ and $R^2$ are independently selected from hydrogen, methyl, and chloro;

$R^3$ is hydrogen, $C_{1-3}$ alkyl, or $C_{1-3}$ fluorinated alkyl;

n is 0, 1, or 2; and $R^4$ is at the meta-, ortho-, or para-position and is independently selected from choloro, hydroxyl, methyl, and methoxy (—$OCH_3$), "independently" meaning that where n is 2, the $R^4$ substituents may be the same or different.

Examples of $R^3$ substituents are: methyl, ethyl, propyl, isopropyl, perfluoromethyl, difluoromethyl, fluoromethyl, perfluoroethyl, tetrafluoroethyl, trifluoroethyl, difluoroethyl, fluoroethyl, perfluoropropyl, etc.

The present invention further provides isolated filovirus entry inhibitor compounds of the formula:

J-1

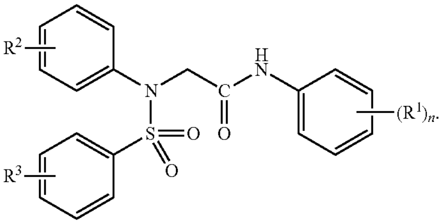

wherein n is 0, 1, or 2;

$R^1$ is at the meta-, ortho-, or para-position and is independently selected from $C_{1-2}$ alkyl, $C_{1-2}$alkoxy, chloro, fluoro, and phenyl, "independently" meaning that where n is 2, the $R^1$ substituents may be the same or different;

$R^2$ is at the meta-, ortho-, or para-position and is selected from hydrogen, $C_{1-2}$ alkyl, $C_{1-2}$ alkoxy, chloro, and fluoro; and $R^3$ is at the meta-, ortho-, or para-position and is selected from hydrogen, $C_{1-2}$ alkyl, and $C_{1-2}$ alkoxy.

The present invention further provides isolated filovirus entry inhibitor compounds of the formula:

K-1

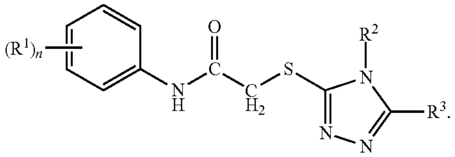

wherein n is 0, 1, or 2;

$R^1$ is at the meta-, ortho-, or para-position and is independently selected from $C_{1-2}$ alkyl, $C_{1-2}$alkoxy, $C_{1-2}$ fluorinated alkyl (e.g., perfluoromethyl, difluoromethyl, fluoromethyl, perfluoroethyl, tetrafluoroethyl, trifluoroethyl, difluoroethyl, fluoroethyl), chloro, and fluoro, "independently" meaning that where n is 2, the $R^1$ substituents may be the same or different;

$R^2$ is hydrogen, $C_{1-3}$ alkyl, phenyl, or toluoyl; and $R^3$ is a substituted 2-benzofuranyl or phenoxymethylene radical of the formula:

K-2

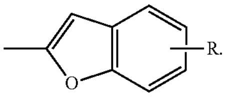

K-3

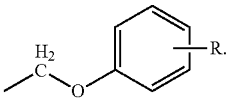

wherein R may be at any ring position and is selected from hydrogen, amino, methylamino, dimethylamino, methyl, and methoxy. Preferred R substituents include the following structures:

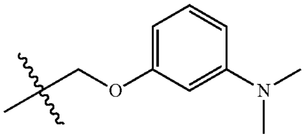
,
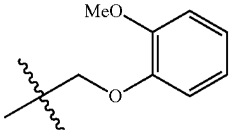
,
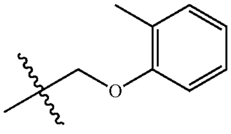
,
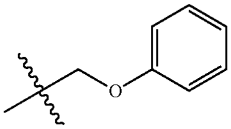
, and
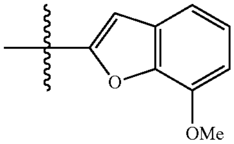
.

The foregoing compounds were identified by assays showing specific inhibition of the entry of HIV-based EBOV pseudotype virus (HIV/EBOV-GP). Selected compounds were additionally tested for inhibition of Marburg filovirus (MARV) using pseudotype MARV virus also having a HIV backbone (HIV/MARV-GP) and showed effective inhibition, indicating that a filovirus GP-mediated entry inhibitor compound according to this invention can be an effective inhibitor of many filovirus species.

Filovirus inhibitory properties discovered for the compounds of the invention are set forth in Tables 2-8, and FIGS. 5-9 infra. Inhibitor compounds were identified as inhibiting infection of HIV-based EBOV pseudotype virus (HIV/EBOV-GP) by at least 90% at a concentration of 25 μM using a luciferase reporter gene assay. Compounds inhibiting infection of HIV/EBOV-GP by less than 90% or with a $CC_{50}$ less than 25 μM are not generally useful as filovirus entry inhibitor in the compositions and methods described herein.

In a preferred embodiment, a filovirus entry inhibitor compound useful in the compositions and methods described herein inhibits HIV/VSV-G infection by less than 50% at a 25 μM concentration as measured in the HIV/VSV-G counter screen described herein. Preferably, the filovirus entry inhibitor compound inhibits HIV/VSV-G infection by less than 50%, 40%, 30%, 20%, or most preferably less than 10% at a 25 μM concentration.

In a particularly preferred embodiment, a filovirus entry inhibitor compound useful in the compositions and methods described herein has an $IC_{50}$ of less than 20 μM as measured in a recombinant Zaire EBOV expressing green fluorescent protein (GFP-ZEBOV) (as a reporter for virus replication) assay described herein (or comparable assay) and also has a relatively low cytotoxicity toward human cells, such as a $CC_{50}$ value of greater than or equal to 25 μM ($CC_{50} \geq 25$ μM) as measured in a standard cytotoxicity assay as described herein or as employed in the pharmaceutical field for antivirals. Such standard cytotoxicity assays may employ any mammalian cell typically employed in cytotoxicity assays for antivirals, including but not limited to, Chinese hamster ovary (CHO) cells, Vero (African green monkey kidney) cells, HeLa cells, Hep-G2 (human hepatocellular carcinoma) cells, human embryonic kidney (HEK) 293 cells, 293T cells, 293FT cells (Invitrogen), BHK (newborn hamster kidney) cells, COS cells, and the like.

In another embodiment, a Filovirus entry inhibitor compound useful in the compositions and methods described herein is selected from the group of inhibitor compounds consisting of

A.

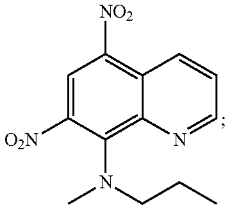
;

B.

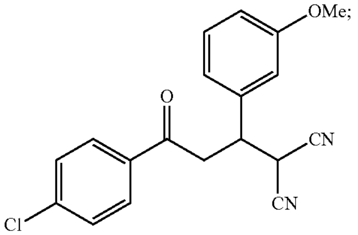
;

C.

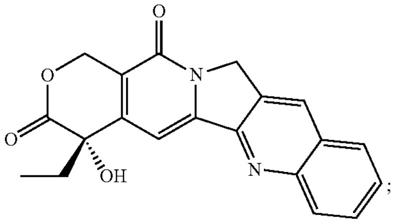
;

D.

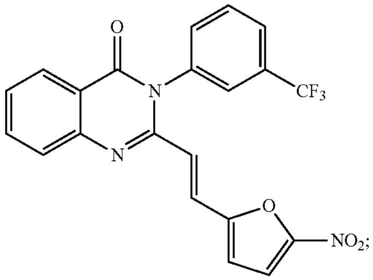
;

-continued

E.

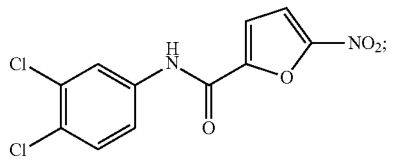

F.

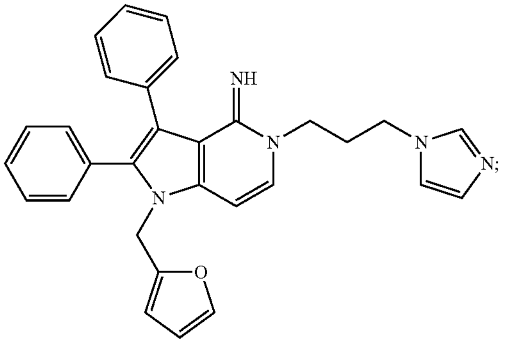

G.

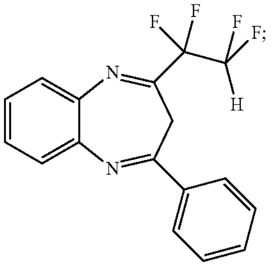

H.

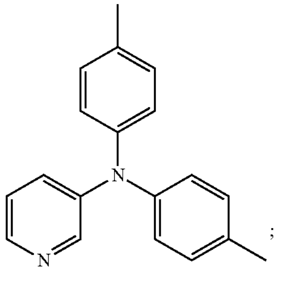

I.

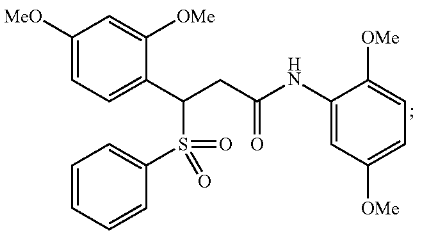

-continued

J.

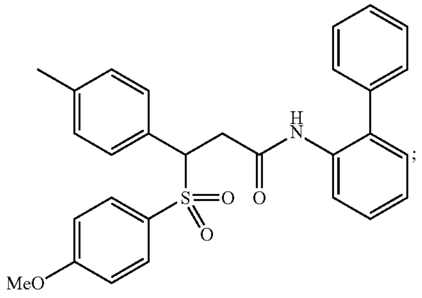

K.

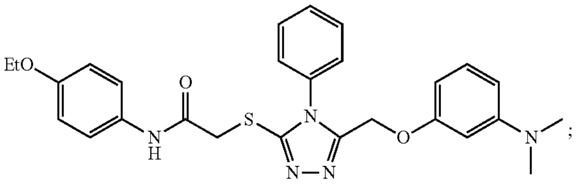

or is selected from isolated filovirus entry inhibitor compounds of the formula:

G-1

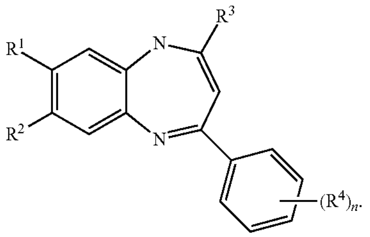

wherein $R^1$ and $R^2$ are independently selected from hydrogen, methyl, and chloro;

$R^3$ is hydrogen, $C_{1-3}$ alkyl (for example, methyl, ethyl, propyl, isopropyl), or $C_{1-3}$ fluorinated alkyl (for example, perfluoromethyl, difluoromethyl, fluoromethyl, perfluoroethyl, tetrafluoroethyl, trifluoroethyl, difluoroethyl, fluoroethyl, perfluoropropyl, etc.);

n is 0, 1, or 2; and $R^4$ is at the meta-, ortho-, or para-position and is independently selected from choloro, hydroxyl, methyl, and methoxy (—$OCH_3$), "independently" meaning that where n is 2, the $R^4$ substituents may be the same or different;

or is selected from isolated filovirus entry inhibitor compounds of the formula:

J-1

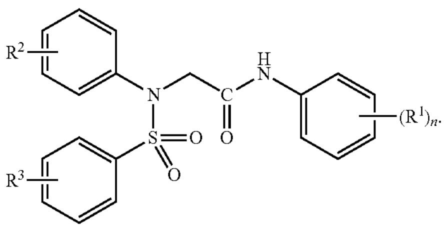

wherein n is 0, 1, or 2;

$R^1$ is at the meta-, ortho-, or para-position and is independently selected from $C_{1-2}$ alkyl, $C_{1-2}$ alkoxy, chloro, fluoro, and phenyl, "independently" meaning that where n is 2, the $R^1$ substituents may be the same or different;

$R^2$ is at the meta-, ortho-, or para-position and is selected from hydrogen, $C_{1-2}$ alkyl, $C_{1-2}$ alkoxy, chloro, and fluoro; and $R^3$ is at the meta-, ortho-, or para-position and is selected from hydrogen, $C_{1-2}$ alkyl, and $C_{1-2}$ alkoxy;

or is selected from filovirus entry inhibitor compounds of the formula:

K-1

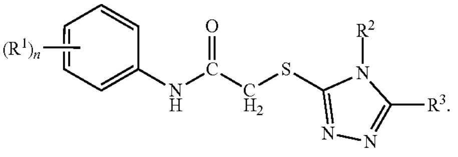

wherein n is 0, 1, or 2;

$R^1$ is at the meta-, ortho-, or para-position and is independently selected from $C_{1-2}$ alkyl, $C_{1-2}$ alkoxy, $C_{1-2}$ fluorinated alkyl (e.g., perfluoromethyl, difluoromethyl, fluoromethyl, perfluoroethyl, tetrafluoroethyl, trifluoroethyl, difluoroethyl, fluoroethyl), chloro, and fluoro, "independently" meaning that where n is 2, the $R^1$ substituents may be the same or different;

$R^2$ is hydrogen, $C_{1-3}$ alkyl, phenyl, or toluoyl; and $R^3$ is a substituted 2-benzofuranyl or phenoxymethylene radical of the formula:

K-2

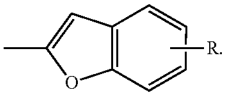

K-3

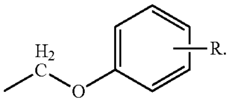

wherein R may be at any ring position and is selected from hydrogen, amino, methylamino, dimethylamino, methyl, and methoxy. Preferred R substituents include the following structures:

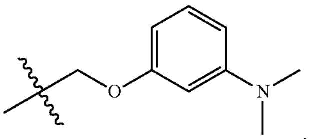
,
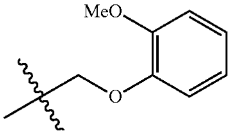
,
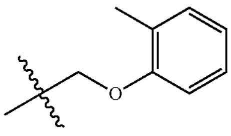
,
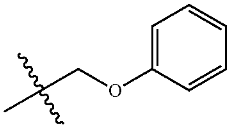
, and

-continued

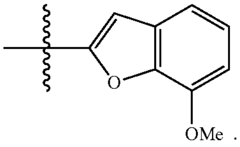

Preferred filovirus entry inhibitor compounds described herein include compound K (Table 5), compound J (Table 5), compound 1 (Table 5), compound G (Tables 3-5), and combinations thereof.

The filovirus entry inhibitor compounds described herein are useful as antiviral agents and may be used to treat filovirus infection, either prophylactically when administered to an individual or a potentially exposed population or therapeutically during the post-infection period. Accordingly, an individual infected with a filovirus or exposed to filovirus infection, especially EBOV infection, may be treated by administering to the individual in need an effective amount of a compound according to the invention, e.g., administering one or more of the following compounds:

A.

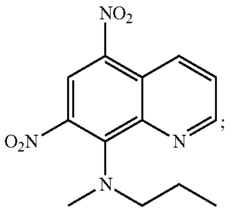

B.

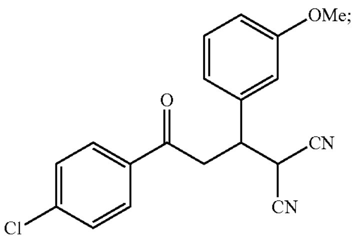

C.

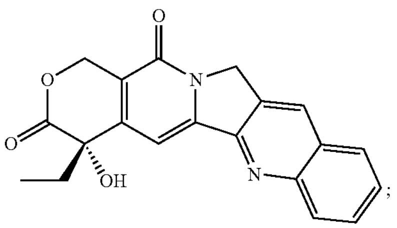

D.

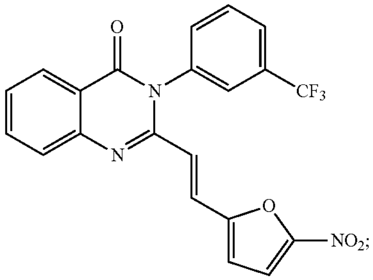

-continued

E.

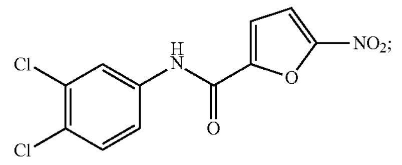

F.

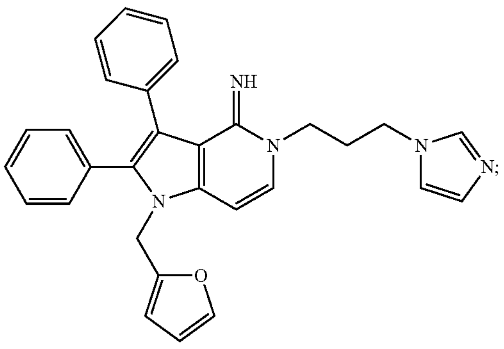

G.

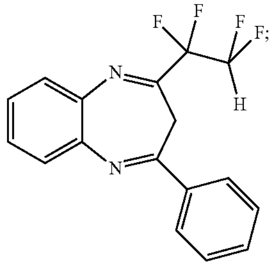

H.

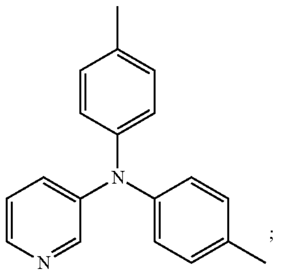

I.

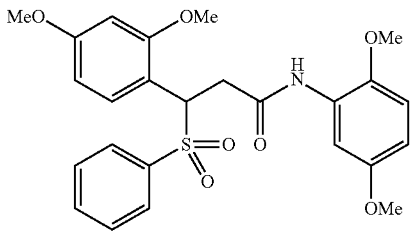

-continued

J.

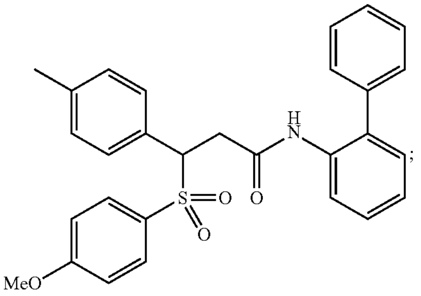

K.

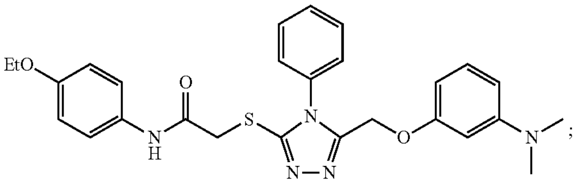

filovirus entry inhibitor compounds of the formula:

G-1

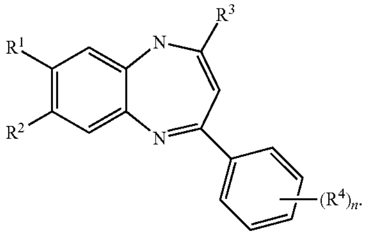

wherein $R^1$ and $R^2$ are independently selected from hydrogen, methyl, and chloro;

$R^3$ is hydrogen, $C_{1-3}$ alkyl, or $C_{1-3}$ fluorinated alkyl (examples of $R^3$ substituents include: methyl, ethyl, propyl, isopropyl, perfluoromethyl, perfluoroethyl, tetrafluoroethyl, trifluoroethyl, difluoroethyl, fluoroethyl; perfluoropropyl, etc.);

n is 0, 1, or 2; and $R^4$ is at the meta-, ortho-, or para-position and is independently selected from choloro, hydroxyl, methyl, and methoxy (—$OCH_3$), "independently" meaning that where n is 2, the $R^4$ substituents may be the same or different;

filovirus entry inhibitor compounds of the formula:

J-1

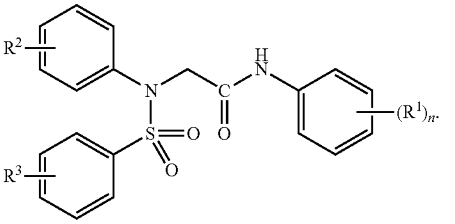

wherein n is 0, 1, or 2;

$R^1$ is at the meta-, ortho-, or para-position and is independently selected from $C_{1-2}$ alkyl, $C_{1-2}$ alkoxy, chloro, fluoro, and phenyl, "independently" meaning that where n is 2, the $R^1$ substituents may be the same or different;

$R^2$ is at the meta-, ortho-, or para-position and is selected from hydrogen, $C_{1-2}$ alkyl, $C_{1-2}$ alkoxy, chloro, and fluoro; and $R^3$ is at the meta-, ortho-, or para-position and is selected from hydrogen, $C_{1-2}$ alkyl, and $C_{1-2}$ alkoxy;

and filovirus entry inhibitor compounds of the formula:

K-1

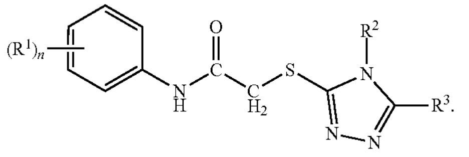

wherein n is 0, 1, or 2;

$R^1$ is at the meta-, ortho-, or para-position and is independently selected from $C_{1-2}$ alkyl, $C_{1-2}$alkoxy, $C_{1-2}$ fluorinated alkyl (e.g., perfluoromethyl, perfluoroethyl, tetrafluoroethyl, etc.), chloro, and fluoro, "independently" meaning that where n is 2, the $R^1$ substituents may be the same or different;

$R^2$ is hydrogen, $C_{1-3}$ alkyl, phenyl, or toluoyl; and $R^3$ is a substituted 2-benzofuranyl or phenoxymethylene radical of the formula:

K-2

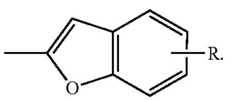

K-3

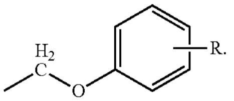

wherein R may be at any ring position and is selected from hydrogen, amino, methylamino, dimethylamino, methyl, and methoxy. Preferred R substituents include the following structures:

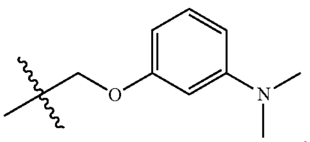
,
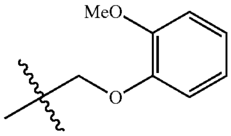
,
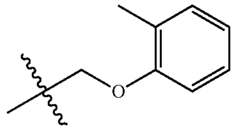
,
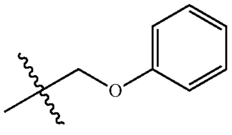
, and
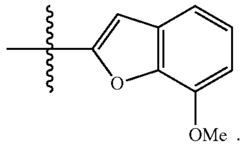
.

Use of one or more or a combination of the above compounds to inhibit filovirus entry is contemplated herein. Especially, use of one or more or a combination of the above compounds to treat EBOV or MARV infection is contemplated herein. In particular, use of one or more or a combination of the above compounds for the treatment of infection of EBOV species Ivory Coast, Sudan, Zaire, Bundibugyo, and/or Reston is advantageously carried out by following the teachings herein.

Use of one or more or a combination of the above compounds to prepare a medicament for treating filovirus infection is contemplated herein. Especially, use of one or more or a combination of the above compounds for preparing a pharmaceutical composition to treat EBOV or MARV infection is contemplated herein. In particular, use of one or more or a combination of the above compounds for the preparation of a medicament for use to treat infection of EBOV species Ivory Coast, Sudan, Zaire, Bundibugyo, and/or Reston is advantageously carried out by following the teachings herein.

The present invention also provides pharmaceutical compositions containing one or more of the filovirus entry inhibitor compounds disclosed herein and a pharmaceutically acceptable carrier or excipient. The use of one or more of the filovirus entry inhibitor compounds in the preparation of a medicament for combating filovirus infection is disclosed.

In yet another embodiment, a composition comprising a filovirus entry inhibitor or a combination of filovirus entry inhibitors described herein may also comprise a second agent (second active ingredient, second active agent) that possesses a desired therapeutic or prophylactic activity other than that of filovirus entry inhibition. Such a second active agent includes, but is not limited to, an antibiotic, an antibody, an additional antiviral agent, an anticancer agent, an analgesic (e.g., a non-steroidal anti-inflammatory drug (NSAID), acetaminophen, an opioid, a COX-2 inhibitor), an immunostimulatory agent (e.g., a cytokine), a hormone (natural or synthetic), a central nervous system (CNS) stimulant, an anti-emetic agent, an anti-histamine, an erythropoietin, a complement stimulating agent, a sedative, a muscle relaxant agent, an anesthetic agent, an anticonvulsive agent, an antidepressant, an antipsychotic agent, and combinations thereof.

Compositions comprising a filovirus entry inhibitor described herein may be formulated for administration to an individual (human or other animal) by any of a variety of routes including, but not limited to, intravenous, intramuscular, subcutaneous, intra-arterial, parenteral, intraperitoneal, sublingual (under the tongue), buccal (cheek), oral (for swallowing), topical (epidermis), transdermal (absorption through skin and lower dermal layers to underlying vasculature), nasal (nasal mucosa), intrapulmonary (lungs), intrauterine, vaginal, intracervical, rectal, intraretinal, intraspinal, intrasynovial, intrathoracic, intrarenal, nasojejunal, and intraduodenal.

In other embodiments, filovirus entry inhibitor compounds described herein are useful as antiviral agents, used individually or in combination with other filovirus entry inhibitor compounds described herein or antivirals known in the art, as topical antiviral solutions, for example, soaps, gels, sprays, aerosols, etc.

until use. Each aliquot was thawed only once for use in a single round of replication. HIV/LASV-GP, HIV/LCMV-GP, HIV/MACV-GP and HIV/HA(H5) pseudotype viruses were also prepared in similar fashion, for counter testing using the same Env-deficient HIV vector as described in Radoshitzky et al., *Nature,* 446:92-6 (2007). High throughput screening of combinatorial chemical libraries using pseudotype virus was performed in 96 well plates. The final concentration of test compound was 25 μM while the final concentration of DMSO in all wells was maintained at 1%. Low passage 293T cell monolayers were infected with 100 μl of p24 normalized HIV/EBOV-GP pseudotype virus containing 8 μg/ml polybrene in the presence of test compounds. After 5 hours, the inoculum was removed, the cells were washed briefly and then incubated for 72 hours. Prior to each screening, each batch of the viral preparation was titrated to determine the amount of virus required to infect the target cells, so that a relatively high luciferase activity could be recorded while still remaining in a linear response range ($10^5$-$10^6$ RLU). Infection was quantified using the Britelite Plus™ assay system (Perkin Elmer) in a Wallac EnVision 2102 Multilabel Reader (Perkin Elmer, MA). Test compounds were in DMSO solutions with 80 compounds per plate. Decreased luciferase activity indicated inhibition of viral entry activity. Controls were also included in each plate; 8 wells for 0% inhibition (DMSO only, maximum signal=positive control) and 8 wells for 100% inhibition (e.g., E-64 for EBOV, minimum signal=negative control). The percent inhibition was calculated as:

$$\frac{[RLU^{*}\text{ in the presence of compound}] - [RLU\text{ of negative control}]}{[RLU\text{ of positive control (without any inhibitor)}] - [RLU\text{ of negative control}]} \times 100\%$$

$*\,RLU$ = relative luciferase units

Compounds showing >90% virus inhibition in this viral infection assay were considered inhibitors and analyzed further.

Figure 3:
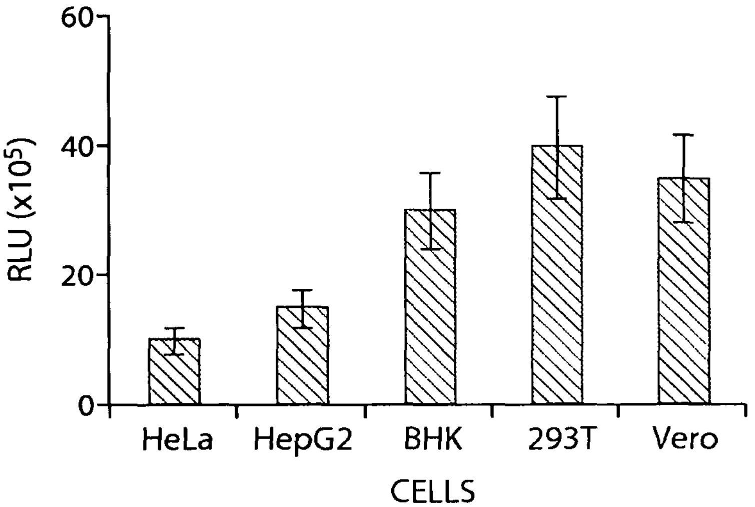

FIG. 3 is a graph showing the infectivity of HIV/EBOV-GP pseudotype virus in different mammalian cells lines. Vero, 293T, HeLa, HepG2, and BHK cell lines were infected with 100 μl of p24 normalized HIV/EBOV-GP pseudotype virus. Following infection, the cells were washed and incubated at 37° C. for 48 hours. Cells were then lysed and luciferase activity was measured, with the maximum activity to background ratio obtained with the 293T cell line.

FIG. 4 is a workflow diagram illustrating the selection process for filovirus inhibitor compounds according to the invention. From an initial composite collection of 100,500 small molecule compounds and natural products at 25 μM concentration, compounds showing greater than 90% inhibition of infection in a HIV/EBOV-GP pseudotype virus assay in 293T cells were subjected to a secondary counter screen in a HIV/VSV-G pseudotype virus infection assay. Compounds showing specific inhibition of EBOV-GP-mediated infectivity were further tested for cytotoxicity in 293T cells. Compounds proving to have low cytotoxicity ($CC_{50}$ greater than 25 μM) were either synthesized or reordered from commercial suppliers and their inhibitory properties reconfirmed. Finally, reconfirmed compounds were tested against infectious recombinant Ebola virus, and those having a 50% inhibitory concentration of 20 μM or less ($IC_{50}$≤20 μM) were considered filovirus viral entry inhibitors.

Figure 5:
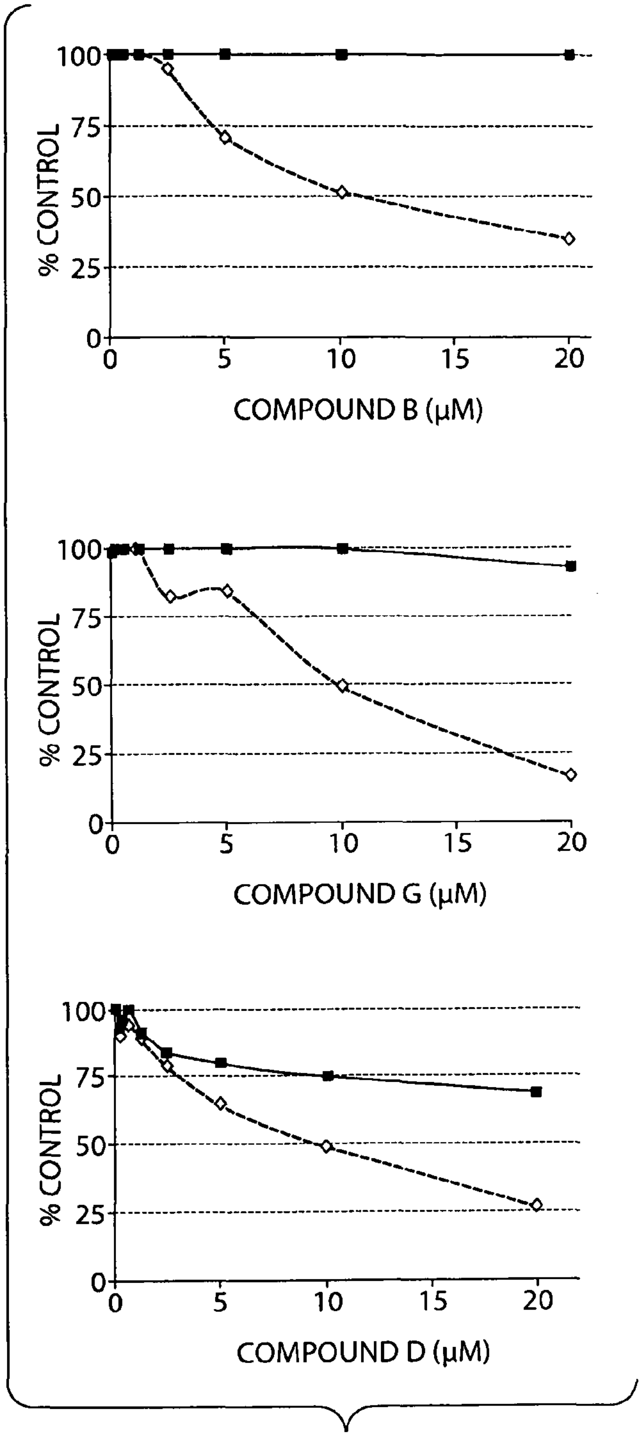
Figure 6:
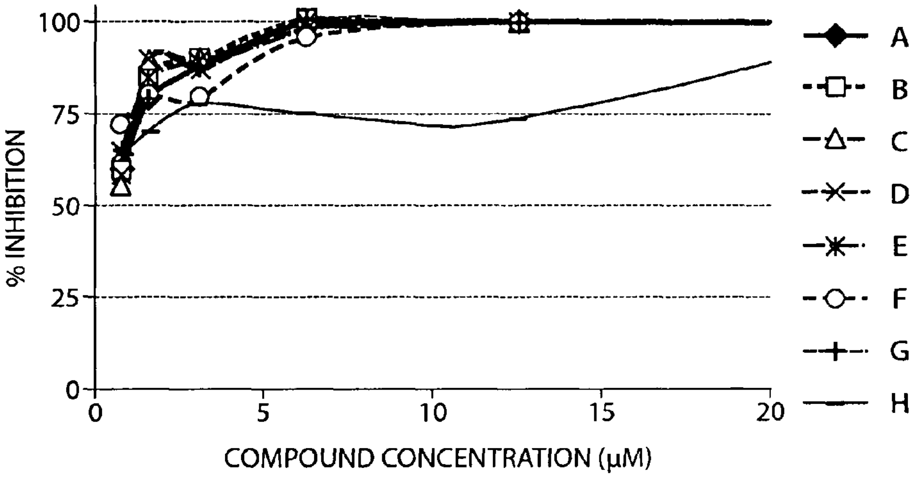

FIG. 5 presents graphs showing the inhibition of infection (◇) and cell toxicity (■) of the confirmed hit compounds B, D, and G (see Example 4). GFP-EBOV was incubated with Vero E6 cells at a multiplicity of infection (MOI) of 1 for 1 hour in the presence or absence of inhibitor compounds in dose dependent manner. Virus was removed after 1 hour, cells were washed in PBS, and incubated for 48 hours, then the percentage of GFP-expressing cells was measured. Similarly, the effect of the compounds on Vero cell cytotoxicity was measured. The diamonds represent inhibitory GFP-EBOV infection activity while the squares represent cytotoxicity FIG. 6 is a graph showing the inhibitory effect of the confirmed inhibitor compounds A-H from Example 4 on pseudotype virus expressing MARV GP. Vero E6 cells ($8\times10^3$ cells/well) were seeded in ninety six-well plates 1 day prior to infection. 100 μl of p24 normalized HIV/MARV-GP pseudotype virus were pre-incubated with the eight confirmed hit compounds from Example 4 in dose dependent manner for 5 hours. Following incubation, the cells were washed and fresh medium was added to the wells and incubated at 37° C. for 48 hours. Cells were then lysed in 100 μl of Britelite® (Perkin-Elmer, Boston, Mass.) solution and luciferase activity was measured. Decrease in luciferase activity indicated inhibition of infectivity. The results show that all of the compounds tested strongly inhibited virus infection at low concentration (e.g., most compounds completely inhibited infection (100% inhibition) at around 7.5 μM) and all of the compounds showed above 90% inhibition at 20 μM.

Figure 7:
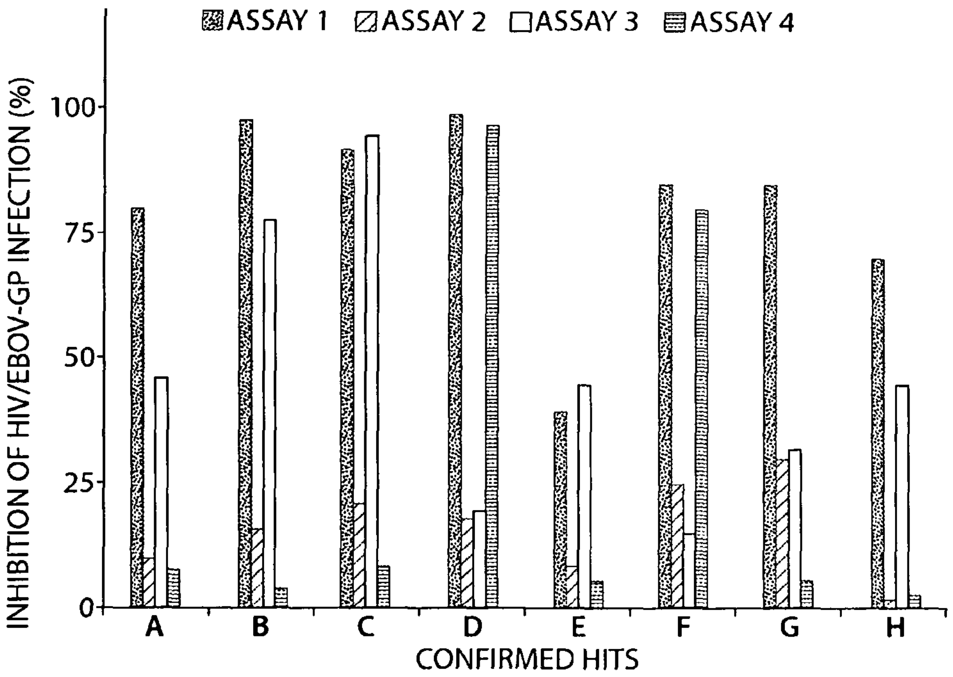

FIG. 7 is a graph showing the results of four separate cell surface blocking analysis experiments. A series of experiments was performed with the HIV/EBOV-GP pseudotype virus to determine the ability of inhibitor compounds A-H from Example 4 to bind with host cell surface receptors and/or viral GP to block viral entry into target cells. 293T cells were infected with HIV/EBOV-GP under different conditions: Assay 1, the inhibitor compounds were added during the pseudotype virus infection; Assay 2, the inhibitor compounds were added after infection; Assay 3, the inhibitor compounds were pre-incubated with the virus for 1 hour before adding the mixture to the target 293T cells; and Assay 4, the inhibitor compounds were pre-incubated with 293T cells at 4° C. before HIV/EBOV-GP virus is added to the cells.

In Assay 1, six of the inhibitor compounds displayed >75% inhibition in antiviral activity when added during the virus infection phase of the assay. However, the compounds exhibited much less activity (<30%) when added after the infection phase of the assay (Assay 2), as would be expected for inhibitors of viral entry.

In Assay 3, inhibitor compounds 2 and 3 displayed an inhibition of HIV/EBOV-GP infection >75%. At the 37° C. incubation temperature normal recycling of the host membrane receptors will occur. Therefore, coupled with the results described above, these data suggest inhibition with inhibitor compounds 2 and 3 may be due to binding of the inhibitor with EBOV-GP, preventing virus attachment to 293T cell surface receptors and thereby inhibiting virus entry.

Assay 4 was conducted to determine whether the inhibitor compounds act as "receptor antagonists". 293T cells were cooled to 4° C., the eight inhibitor compounds were then added to wells at a 10 μM concentration in ice cold DMEM, and cells incubated for 60 minutes on ice. The incubation at low temperature reduces receptor-mediated uptake of the compounds by the cells. As shown in Assay 4 (fourth bars), inhibitor compounds 4 and 6 displayed inhibition of infection >75% in this assay, suggesting that they may be binding to the cellular receptors and thereby inhibiting EBOV entry.

Figure 8:
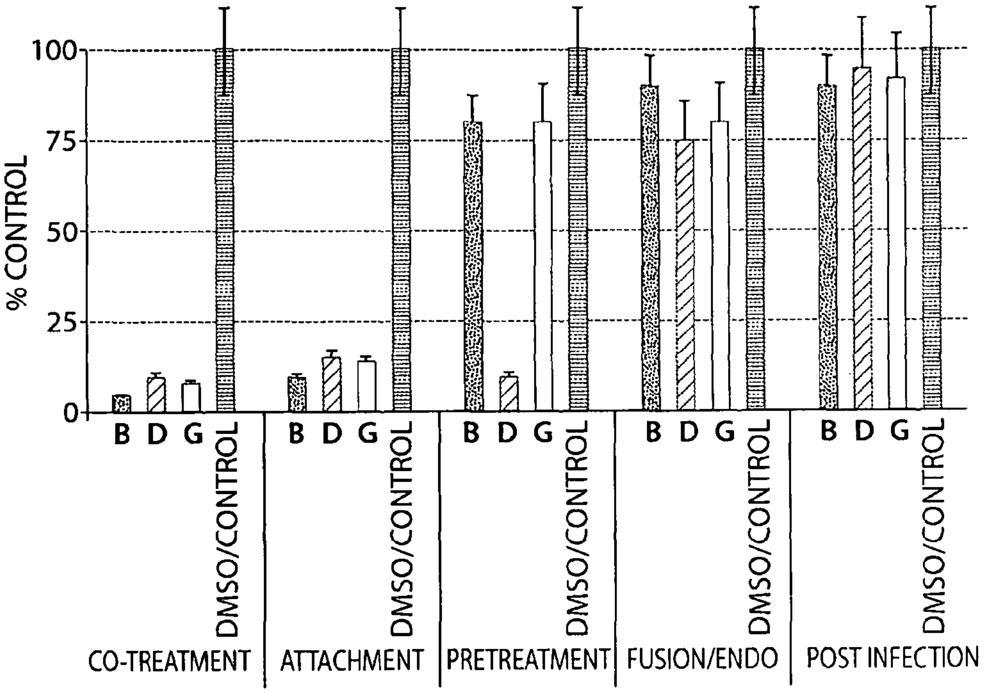

FIG. 8 is a graph showing the ability of selected compounds B, D, and G to inhibit binding/attachment of HIV/EBOV-GP with cellular receptors. 293T cells were infected with HIV/EBOV-GP in presence of 10 μM of one of the selected compounds under different conditions (Co-treatment, Attachment, Pretreatment, Fusion/Endocytosis, and Postinfection). In the co-treatment, the selected compounds were added during the infection and incubated at 37° C. for virus adsorption; in the Attachment condition, the inhibitor compounds were added during the infection and incubated at 4° C.; in the Pretreatment condition, inhibitor compounds were preincubated with 293T cells at 4° C. before HIV/EBOV-GP is added to the cells; in the Fusion/Endocytosis condition, virus was adsorbed at 4° C., followed by addition of the inhibitor compounds and further incubation for 2 h at 37° C.; and in the Postinfection condition, inhibitor compounds were added to cells after incubation with the virus.

Figure 9:
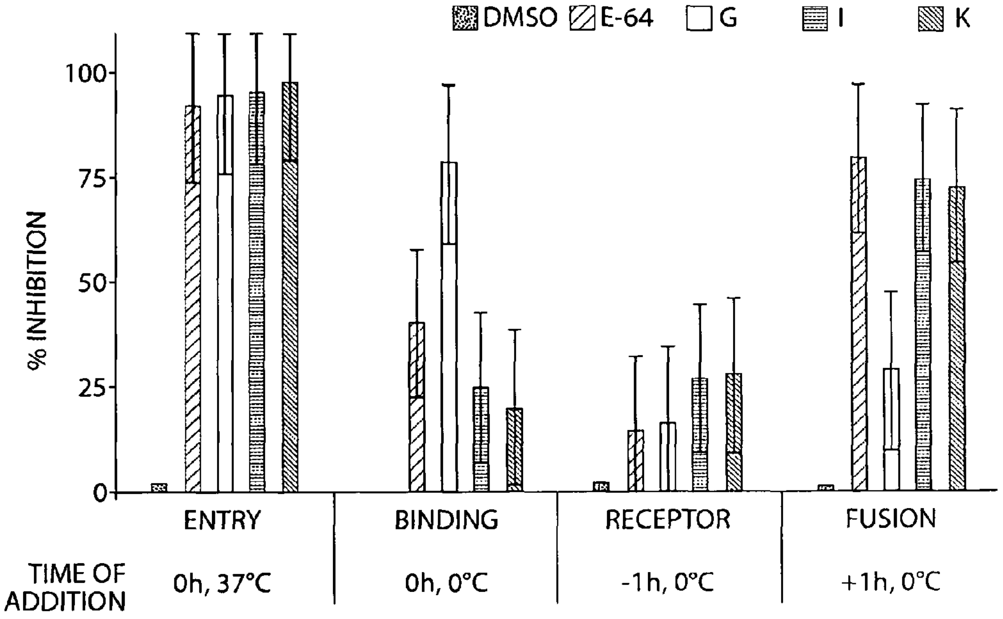

FIG. 9 is a graph showing the results of time of addition studies. Selected compounds G, I, and K were added at 1 hour before infection (−1 h), during adsorption (0 h), and 1 hour after infection (+1 h) of HIV/EBOV-GP pseudotype virus. Controls consisted of DMSO (negative control) and E-64 (positive control), a pan-caspase inhibitor that inhibits EBOV infection. Representative compounds G, I, and K are shown. Compound G was active (>75% inhibition) when added at time 0 at 0° C., but not at −1 hr or +1 hr, suggesting it may act by interference with virus binding. In contrast, the aminoacetamide sulfonamide series compounds I and K, were active when added after virus infection (+1 h) but not at −1 hr or 0 hr, indicating those compounds may act by interference with the fusion process.

DETAILED DESCRIPTION OF THE INVENTION

The invention provides organic compounds that inhibit viral glycoprotein (GP)-mediated entry of a filovirus into a host cell. Envelope glycoprotein is the sole envelope protein making up the virion surface spikes in filoviruses, which bind to the host cellular receptor(s) and mediate viral entry. Viral glycoprotein (GP)-mediated entry of a filovirus is thus a critical factor in filovirus infectivity in an individual (human or other animal) and is particularly critical to EBOV and MARV infections.

In order that the invention may be more clearly understood, the following abbreviations and terms are used as defined below.

"Filovirus" as defined herein refers to viruses of the Mononegavirales order, specifically, the Filoviridae family of viruses, which contains two specific genera, Ebola virus (EBOV) (also referred to in the art as "Ebola-like viruses") and Marburg virus (MARV) (also referred to in the art as "Marburg-like viruses"). The genera EBOV is further subdivided into four distinct African species (Ivory Coast, Sudan, Zaire, and Bundibugyo) and a single Asian species (Reston).

Abbreviations for various substituents (side groups, radicals) of organic molecules are those commonly used in organic chemistry. Such abbreviations may include "shorthand" forms of such substituents. For example, "Me" and "Et" are abbreviations used to indicate methyl ($CH_3$—) and ethyl ($CH_3CH_2$—) groups, respectively; and "OMe" and "OEt" indicate methoxy ($CH_3O$—) and ethoxy ($CH_3CH_2O$—), respectively. Hydrogen atoms are not always shown in organic molecular structures or may be only selectively shown in some structures, as the presence and location of hydrogen atoms in organic molecular structures are understood and known by persons skilled in the art. Likewise, carbon atoms are not always specifically abbreviated with "C", as the presence and location of carbon atoms, e.g., between or at the end of bonds, in structural diagrams are known and understood by persons skilled in the art. Minutes are commonly abbreviated as "min"; hours are commonly abbreviated as "hr" or "h".

A composition or method described herein as "comprising" one or more named elements or steps is open-ended, meaning that the named elements or steps are essential, but other elements or steps may be added within the scope of the composition or method. To avoid prolixity, it is also understood that any composition or method described as "comprising" (or which "comprises") one or more named elements or steps also describes the corresponding, more limited composition or method "consisting essentially of" (or which "consists essentially of") the same named elements or steps, meaning that the composition or method includes the named essential elements or steps and may also include additional elements or steps that do not materially affect the basic and novel characteristic(s) of the composition or method. It is also understood that any composition or method described herein as "comprising" or "consisting essentially of" one or more named elements or steps also describes the corresponding, more limited, and closed-ended composition or method "consisting of" (or "consists of") the named elements or steps to the exclusion of any other unnamed element or step. In any composition or method disclosed herein, known or disclosed equivalents of any named essential element or step may be substituted for that element or step. It is also understood that an element or step "selected from the group consisting of" refers to one or more of the elements or steps in the list that follows, including combinations of any two or more of the listed elements or steps.

The terms "filovirus entry inhibitor compound", "filovirus GP-mediated entry inhibitor compound", and "HIV/EBOV-GP entry inhibitors", as used herein denote compounds exhibiting the ability to specifically inhibit infection of filoviruses or surrogate pseudotype viruses such as HIV/EBOV-GP described herein by at least 90% at a concentration of 25 μM using an infectivity assay, e.g., a luciferase reporter gene assay such as described below.

In the context of therapeutic use of the filovirus entry inhibitor compounds described herein, the terms "treatment", "to treat", or "treating" will refer to any use of the filovirus entry inhibitor compounds calculated or intended to arrest, inhibit, prevent or reduce the infection of a host cell with a filovirus. Thus, treating an individual may be carried out after any diagnosis indicating possible filovirus infection, i.e., whether an infection by a particular filovirus has been confirmed or whether the possibility of infection is only suspected, for example, after an individual's exposure to the filovirus or to another individual infected by the filovirus. It is also recognized that because the inhibitors of the present invention affect the initial introduction of virus into host cells, and thus block or decrease the viral replication resulting from infection, the viral entry inhibitors disclosed herein will also be useful for prevention of disease in those exposed to infection but whose infection or development of disease has not been confirmed or diagnosed. Also, because the compounds of the present invention inhibit viral entry, it will be understood that elimination of the viral infection will be accomplished by the host's own immune system or immune effector cells. Thus, it is contemplated that the compounds of the present invention will often be routinely combined with other active ingredients such as antibiotics, antibodies, other antiviral agents, anticancer agents, analgesics (e.g., a non-steroidal anti-inflammatory drug (NSAID), acetaminophen, opioids, COX-2 inhibitors), immunostimulatory agents (e.g., cytokines or a synthetic immunostimulatory organic molecules), hormones (natural, synthetic, or semi-synthetic), central nervous system (CNS) stimulants, antiemetic agents, anti-histamines, erythropoietin, agents that activate complement, sedatives, muscle relaxants, anesthetic agents, anticonvulsive agents, antidepressants, antipsychotic agents, and combinations thereof.

The meaning of other terms will be understood by the context as understood by the skilled practitioner in the art, including the fields of organic chemistry, pharmacology, and virology.

The invention provides specific organic compounds that inhibit filovirus entry, particularly EBOV envelope glycoprotein (GP) mediated viral entry. Putative inhibitors of EBOV and other filoviruses ("hits") were initially identified by screening collections of organic molecules using a HIV-based EBOV pseudotype virus (HIV/EBOV-GP) luciferase reporter assay (see FIG. 2). Compounds showing greater than 90% inhibition of luciferase activity at a 25 μM concentration were designated as a "hit". Most (e.g., greater than 80%) of the initial hits were subsequently eliminated by a counter assay requiring <50% inhibition of luciferase activity at a 25 μM in HIV/VSV-G counter screen. Both the HIV/VSV-G used as a counter screen and the HIV/EBOV-GP used in the initial high throughput screen have the identical HIV backbone, but express different envelop proteins, VSV-G and EBOV-GP, respectively. The screening of the "primary hits" against HIV/VSV-G was performed to determine that the inhibition was specific for filovirus entry (that is, to confirm that the inhibitor compounds were not non-specific, general inhibitors of viruses). Non-specific inhibitor compounds, i.e., showing >50% inhibition of luciferase activity at a 25 μM in the HIV/VSV-G counter screen were discarded. See, Examples 3 and 9, below for details of screening and validation of filovirus entry inhibitors.

A filovirus entry inhibitor compound useful in the compositions and methods of the invention has a structure of a compound in any of Tables 1-8. The compounds preferably have a 50% inhibitory concentration ($IC_{50}$) less than 100 μM, preferably less than 25 μM, as measured in a suitable cell-based infectivity assay, such as the HIV-based EBOV pseudotype virus (HIV/EBOV-GP) infectivity assay using a luciferase reporter gene as described in the examples, infra. Compounds with $IC_{50}$ greater than 100 μM are not generally useful as therapeutic inhibitors in the compositions and methods described herein for administration to humans and other animals.

A filovirus entry inhibitor compound that is particularly useful in the compositions and methods described herein has an $IC_{50}$ of less than 100 μM as measured in an HIV-based EBOV pseudotype virus (HIV/EBOV-GP) assay using a luciferase reporter gene as described (or a comparable infectivity assay) and also has a relatively low cytotoxicity toward mammalian cells, such as a $CC_{50}$ value of greater than or equal to 100 μM as measured in a standard cytotoxicity assay as described herein or as employed in the pharmaceutical field for antivirals. Such standard cytotoxocity assays may employ Chinese hamster ovary (CHO) cells, HeLa cells, Hep-G2 cells, human embryonic kidney (HEK) 293 cells, 293T cells, 293FT cells, BHK cells, COS cells or other suitable mammalian cell lines known in the art.

Preferred filovirus entry inhibitor compounds described herein include compounds G, I, J, K (see, e.g., Table 5), and combinations thereof.

The filovirus entry inhibitor compounds described herein are organic compounds that can be either synthesized or ordered from suppliers such as ChemBridge Corporation (San Diego, Calif., USA), Life Chemicals Inc. (Burlington, ON, Canada), ChemDiv Inc. (San Diego, Calif., USA), and Timtec LLC (Newark, Del., USA). Filovirus entry inhibitor compounds as described herein may also be synthesized using established chemistries, and suitable synthesis schemes for the compounds include the following:

The benzodiazepine EBOV entry inhibitor compounds may be synthesized beginning with 3-ketoketones (Scheme 1, below). Thus, acetophenone (1) is lithiated with a strong base, and the resulting enolate is reacted with a simple fluorinated ester (2). The resulting ketoketone is produced as its lithium salt enolate, which is used directly in the following steps.

Scheme 1. Synthesis of fluorinated 1,3-diketones as Li salts.

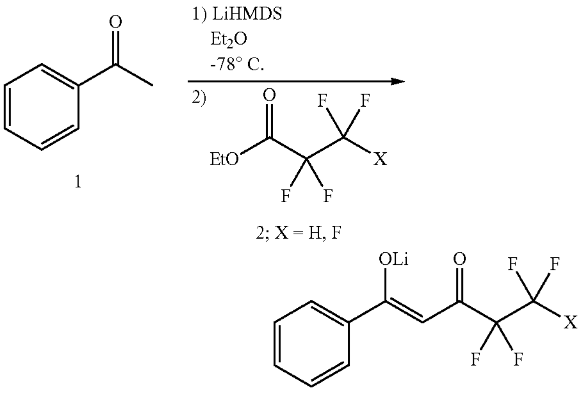

1

2; X = H, F

3; X = H, F

To synthesize the desired benzodiazepines of formula G and G-1 (see, 6 in Scheme 2, below), the enolates above (3) acidified in situ to the corresponding diketones 5 are reacted with o-phenylenediamines (4) under acid catalysis, or microwave irradiation. The benzodiazepines 6 are thus obtained in a single step from the corresponding diamines and diketones.

Scheme 2. Synthesis of benzodiazepines.

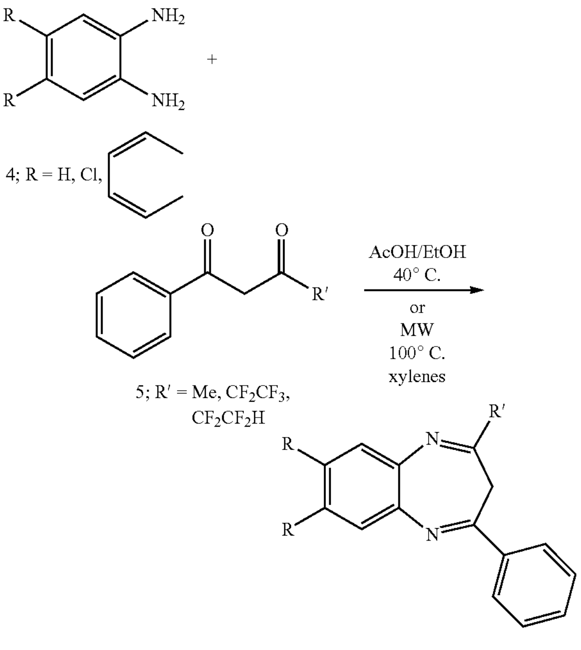

4; R = H, Cl,

5; R' = Me, $CF_2CF_3$, $CF_2CF_2H$

6

The dinitroquinolone inhibitor compound A (8, below) is synthesized in a single step via nucleophilic displacement (Scheme 3). Thus, 8-chloro-5,7-dinitroquinoline (7) is heated with N-methyl(propyl)amine to provide 8.

Scheme 3. Synthesis of amine-substituted dinitroquinolines.

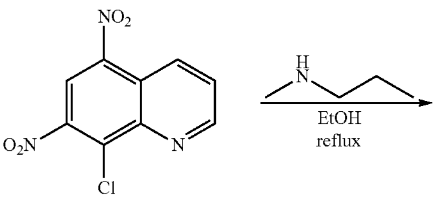

7

-continued

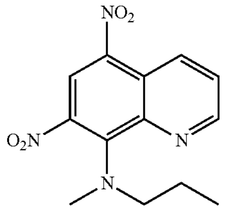

8

The quinazolinone inhibitors (e.g., inhibitor compound formula D) of the general structure 16 (Scheme 4, below) are made in two steps from the commercially available benzoxazine 12 (Scheme 4). The benzoxazine is first heated with an aniline (13) to form 3-phenylquinazolinone derivative 14. This intermediate is then reacted with substituted furan-2-carboxaldehyde 15 in the presence of sodium acetate (NaOAc)/acetic acid (AcOH) to provide the desired quinazolinones 16.

Scheme 4. Synthesis of diaryl quinazolinones.

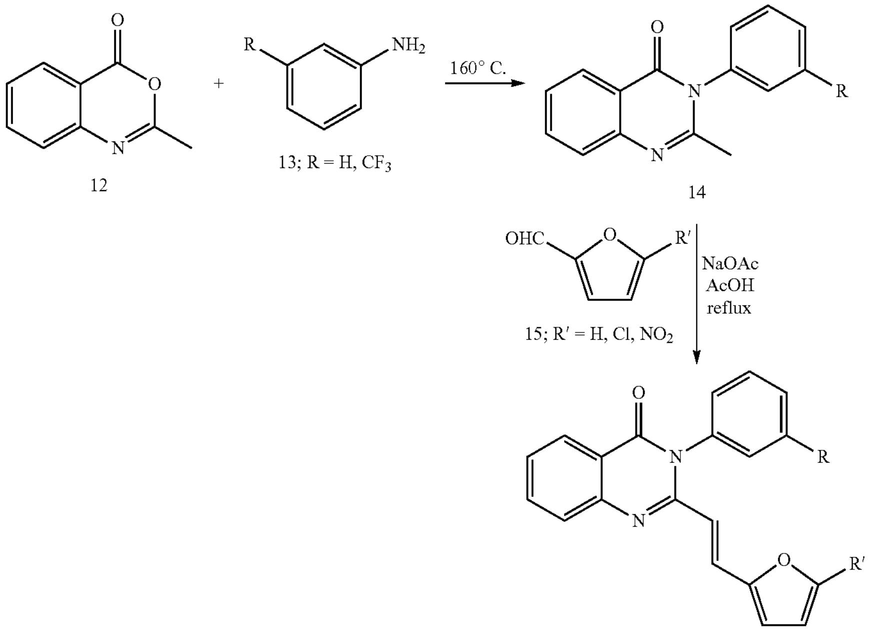

12

13; R = H, $CF_3$

14

15; R′ = H, Cl, $NO_2$

16

The aminoacetamide sulfonamide compounds of formula I, J, and J-1 can be produced in a combinatorial synthesis using solid-phase organic synthesis (SPOS) techniques (Scheme 5, below). An aniline is first attached to a functionalized resin by reductive alkylation. Subsequent addition of linker, second aniline, and sulfonamide moieties provide an immobilized target molecule. The compound is then freed from the resin by treatment with acid to produce the desired aminoacetamide sulfonamides.

Scheme 5. Combinatorial synthesis of aminoacetamide sulfonamides.

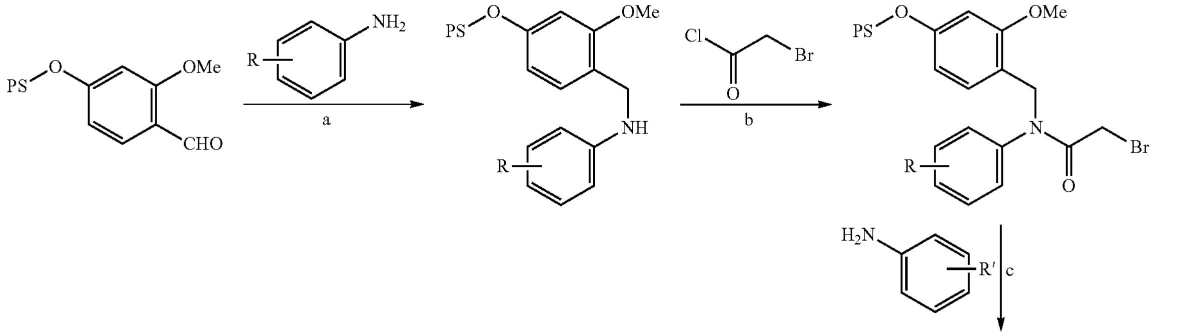

-continued

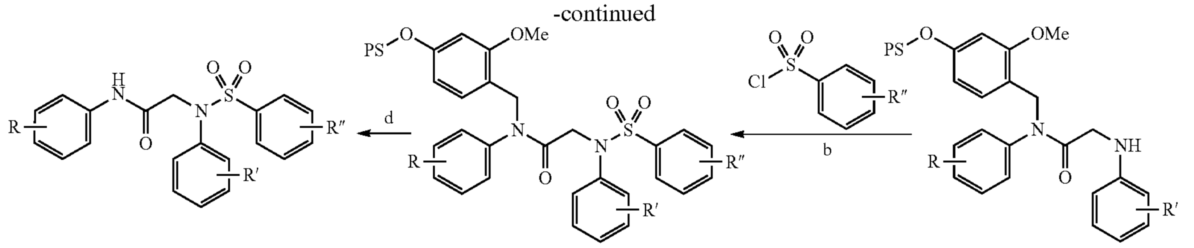

Reagents and conditions: (a) $NaBH_3CN$, AcOH, EtOH; (b) pyridine, $CH_2Cl_2$; (c) DMF, 100° C.; (d) TFA, $CH_2Cl_2$.

The triazole thioethers of formula K and K-1 are produced in a sequential manner shown in Scheme 6, below. A phenol is functionalized with methyl bromoacetate and then converted to the corresponding hydrazide with hydrazine. Addition of an aryl isothiocyanate provides a substituted triazole thiol. This is alkylated with bromoacetic acid, then an aniline is coupled to the acid to provide a series of triazole thioether molecules.

Scheme 6.
Semi-combinatorial synthesis of triazole thioehters.
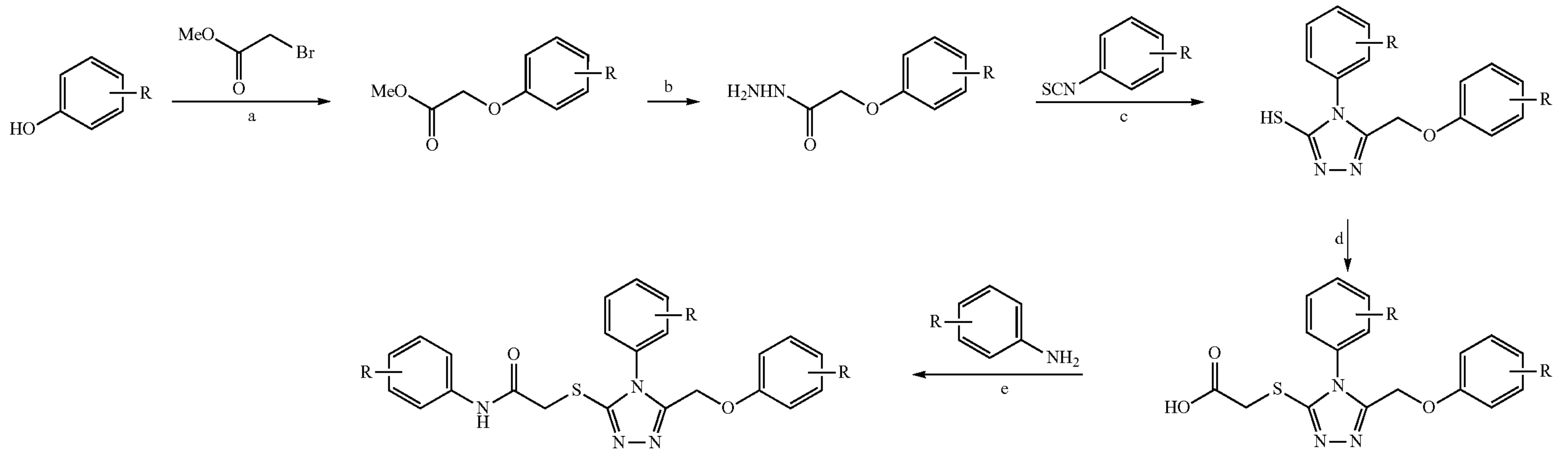
Reagents and conditions: (a) $K_2CO_3$, DMF, 60° C.; (b) hydrazine hydrate, EtOH; (c) DIPEA, $CH_2Cl_2$; (d) bromoacetic acid, DMF, 60° C.; (e) HATU, DIPEA, DMF.

Unless otherwise indicated, it is understood that description of the use of a filovirus entry inhibitor compound in a composition or method also encompasses embodiments wherein a combination of two or more filovirus entry inhibitor compounds are employed as active ingredients providing filovirus entry inhibitory activity in a composition or method of the invention.

Pharmaceutical compositions according to the invention comprise an isolated filovirus entry inhibitor compound as described herein, or a pharmaceutically acceptable salt thereof, as the active ingredient and a pharmaceutically acceptable carrier (or "vehicle"), which may be a liquid, solid, or semi-solid compound. By "pharmaceutically acceptable" is meant that a compound or composition is not biologically, chemically, or in any other way, incompatible with body chemistry and metabolism and also does not adversely affect the filovirus entry inhibitor or any other component that may be present in a composition in such a way that would compromise the desired therapeutic and/or preventative benefit to a patient. Pharmaceutically acceptable carriers useful in the invention include those that are known in the art of preparation of pharmaceutical compositions and include, without limitation, water, physiological pH buffers, physiologically compatible salt solutions (e.g., phosphate buffered saline), and isotonic solutions. Pharmaceutical compositions of the invention may also comprise one or more excipients, i.e., compounds or compositions that contribute or enhance a desirable property in a composition other than the active ingredient.

Various aspects of formulating pharmaceutical compositions, including examples of various excipients, dosages, dosage forms, modes of administration, and the like are known to those skilled in the art of pharmaceutical compositions and also available in standard pharmaceutical texts, such as *Remington's Pharmaceutical Sciences,* 18th edition, Alfonso R. Gennaro, ed. (Mack Publishing Co., Easton, Pa. 1990), *Remington: The Science and Practice of Pharmacy, Volumes* 1 & 2, 19th edition, Alfonso R. Gennaro, ed., (Mack Publishing Co., Easton, Pa. 1995), or other standard texts on preparation of pharmaceutical compositions.

Pharmaceutical compositions may be in any of a variety of dosage forms particularly suited for an intended mode of administration. Such dosage forms, include, but are not limited to, aqueous solutions, suspensions, syrups, elixirs, tablets, lozenges, pills, capsules, powders, films, suppositories, and powders, including inhalable formulations. Preferably, the pharmaceutical composition is in a unit dosage form suitable for single administration of a precise dosage, which may be a fraction or a multiple of a dose that is calculated to produce effective inhibition of filovirus entry.

A composition comprising a filovirus entry inhibitor compound (or combination of filovirus entry inhibitors) described herein may optionally possess a second active ingredient (also referred to as "second agent", "second active agent") that provides one or more other desirable therapeutic or prophylactic activities other than filovirus entry inhibitory activity. Suitable second agents useful in compositions of the invention include, but without limitation, an antibiotic, an antibody, an antiviral agent, an anticancer agent, an analgesic (e.g., a non-steroidal anti-inflammatory drug (NSAID), acetaminophen, an opioid, a COX-2 inhibitor), an immunostimulatory agent (e.g., a cytokine or a synthetic immunostimulatory organic molecule), a hormone (natural, synthetic, or semi-synthetic), a central nervous system (CNS) stimulant, an antiemetic agent, an anti-histamine, an erythropoietin, a complement stimulating agent, a sedative, a muscle relaxant agent, an anesthetic agent, an anticonvulsive agent, an antidepressant, an antipsychotic agent, pluralities of such agents, and combinations thereof.

Pharmaceutical compositions as described herein may be administered to humans and other animals in a manner similar to that used for other known therapeutic or prophylactic agents, and particularly as used for therapeutic antivirals. The dosage to be administered to an individual and the mode of administration will depend on a variety of factors including age, weight, sex, condition of the patient, and genetic factors, and will ultimately be decided by an attending qualified healthcare provider.

Pharmaceutically acceptable salts of filovirus entry inhibitor compounds described herein include those derived from pharmaceutically acceptable inorganic and organic acids and bases. Examples of suitable acids include hydrochloric, hydrobromic, sulfuric, nitric, perchloric, fumaric, maleic, malic, pamoic, phosphoric, glycolic, lactic, salicylic, succinic, toluene-p-sulfonic, tartaric, acetic, citric, methanesulfonic, formic, benzoic, malonic, naphthalene-2-sulfonic, tannic, carboxymethyl cellulose, polylactic, polyglycolic, and benzenesulfonic acids.

The invention may also envision the "quaternization" of any basic nitrogen-containing groups of a compound described herein, provided such quaternization does not destroy the ability of the compound to inhibit filovirus entry. Such quaternization may be especially desirable to enhance solubility. Any basic nitrogen can be quaternized with any of a variety of compounds, including but not limited to, lower (e.g., $C_1$-$C_4$) alkyl halides (e.g., methyl, ethyl, propyl and butyl chloride, bromides, and iodides); dialkyl sulfates (e.g., dimethyl, diethyl, dibutyl and diamyl sulfates); long chain halides (e.g., decyl, lauryl, myristyl and stearyl chlorides, bromides and iodides); and aralkyl halides (e.g., benzyl and phenethyl bromides).

For solid compositions, conventional nontoxic solid carriers may be used including, but not limited to, mannitol, lactose, starch, magnesium stearate, sodium saccharin, talc, cellulose, glucose, sucrose, and magnesium carbonate.

Pharmaceutical compositions may be formulated for administration to a patient by any of a variety of parenteral and non-parenteral routes or modes. Such routes include, without limitation, intravenous, intramuscular, intra-articular, intraperitoneal, intracranial, paravertebral, periarticular, periostal, subcutaneous, intracutaneous, intrasynovial, intrasternal, intrathecal, intralesional, intratracheal, sublingual, pulmonary, topical, rectal, nasal, buccal, vaginal, or via an implanted reservoir. Implanted reservoirs may function by mechanical, osmotic, or other means. Generally and particularly when administration is via an intravenous, intra-arterial, or intramuscular route, a pharmaceutical composition may be given as a bolus, as two or more doses separated in time, or as a constant or non-linear flow infusion.

A pharmaceutical composition may be in the form of a sterile injectable preparation, e.g., as a sterile injectable aqueous solution or an oleaginous suspension. Such preparations may be formulated according to techniques known in the art using suitable dispersing or wetting agents (e.g., polyoxyethylene 20 sorbitan monooleate (also referred to as "polysorbate 80"); TWEEN® 80, ICI Americas, Inc., Bridgewater, N.J.) and suspending agents. Among the acceptable vehicles and solvents that may be employed for injectable formulations are mannitol, water, Ringer's solution, isotonic sodium chloride solution, and a 1,3-butanediol solution. In addition, sterile, fixed oils may be conventionally employed as a solvent or suspending medium. For this purpose, a bland fixed oil may be employed including synthetic mono- or diglycerides. Fatty acids, such as oleic acid and its glyceride derivatives are useful in the preparation of injectables, as are natural pharmaceutically-acceptable oils, including olive oil or castor oil, especially in their polyoxyethylated versions.

A filovirus entry inhibitor described herein may be formulated in any of a variety of orally administrable dosage forms including, but not limited to, capsules, tablets, caplets, pills, films, aqueous solutions, oleaginous suspensions, syrups, or elixirs. In the case of tablets for oral use, carriers, which are commonly used include lactose and corn starch. Lubricating agents, such as magnesium stearate, are also typically added. For oral administration in a capsule form, useful diluents include lactose and dried cornstarch. Capsules, tablets, pills, films, lozenges, and caplets may be formulated for delayed or sustained release.

Tablets and other solid or semi-solid formulations may be prepared that rapidly disintegrate or dissolve in an individual's mouth. Such rapid disintegration or rapid dissolving formulations may eliminate or greatly reduce the use of exogenous water as a swallowing aid. Furthermore, rapid disintegration or rapid dissolve formulations are also particularly useful in treating individuals with swallowing difficulties. For such formulations, a small volume of saliva is usually sufficient to result in tablet disintegration in the oral cavity. The active ingredient (a filovirus entry inhibitor described herein) can then be absorbed, partially or entirely into the circulation from blood vessels underlying the oral mucosa (e.g., sublingual and/or buccal mucosa), or it can be swallowed as a solution to be absorbed from the gastrointestinal tract.

When aqueous suspensions are to be administered orally, whether for absorption by the oral mucosa or absorption via the gut (stomach and intestines), a composition comprising a filovirus entry inhibitor may be advantageously combined with emulsifying and/or suspending agents. Such compositions may be in the form of a liquid, dissolvable film, dissolvable solid (e.g., lozenge), or semi-solid (chewable and digestible). If desired, such orally administrable compositions may also contain one or more other excipients, such as a sweetener, a flavoring agent, a taste-masking agent, a coloring agent, and combinations thereof.

The pharmaceutical compositions comprising a filovirus entry inhibitor as described herein may also be formulated as suppositories for vaginal or rectal administration. Such compositions can be prepared by mixing a filovirus entry inhibitor compound as described herein with a suitable, non-irritating excipient that is solid at room temperature but liquid at body temperature and, therefore, will melt in the appropriate body space to release the filovirus entry inhibitor and any other desired component of the composition. Excipients that are particularly useful in such compositions include, but are not limited to, cocoa butter, beeswax, and polyethylene glycols.

Topical administration of a filovirus entry inhibitor may be useful when the desired treatment involves areas or organs accessible by topical application, such as the epidermis, surface wounds, or areas made accessible during surgery. Carriers for topical administration of a filovirus entry inhibitor described herein include, but are not limited to, mineral oil, liquid petroleum, white petroleum, propylene glycol, polyoxyethylene polyoxypropylene compounds, emulsifying wax, and water. Alternatively, a topical composition comprising a filovirus entry inhibitor as described herein may be formulated with a suitable lotion or cream that contains the inhibitor suspended or dissolved in a suitable carrier to promote absorption of the inhibitor by the upper dermal layers without significant penetration to the lower dermal layers and underlying vasculature. Carriers that are particularly suited for topical administration include, but are not limited to, mineral oil, sorbitan monostearate, polysorbate 60, cetyl esters wax, cetearyl alcohol, 2-octyldodecanol, benzyl alcohol, and water. A filovirus entry inhibitor may also be formulated for topical application as a jelly, gel, or emollient. Topical administration may also be accomplished via a dermal patch.

Persons skilled in the field of topical and transdermal formulations are aware that selection and formulation of various ingredients, such as absorption enhancers, emollients, and other agents, can provide a composition that is particularly suited for topical administration (i.e., staying predominantly on the surface or upper dermal layers with minimal or no absorption by lower dermal layers and underlying vasculature) or transdermal administration (absorption across the upper dermal layers and penetrating to the lower dermal layers and underlying vasculature).

Pharmaceutical compositions comprising a filovirus entry inhibitor as described herein may be formulated for nasal administrations, in which case absorption may occur via the mucous membranes of the nasal passages or the lungs. Such modes of administration typically require that the composition be provided in the form of a powder, solution, or liquid suspension, which is then mixed with a gas (e.g., air, oxygen, nitrogen, or a combination thereof) so as to generate an aerosol or suspension of droplets or particles. Inhalable powder compositions preferably employ a low or non-irritating powder carrier, such as melezitose (melicitose). Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Pharmaceutical compositions described herein may be packaged in a variety of ways appropriate to the dosage form and mode of administration. These include but are not limited to vials, bottles, cans, packets, ampoules, cartons, flexible containers, inhalers, and nebulizers. Such compositions may be packaged for single or multiple administrations from the same container. Kits may be provided comprising a composition, preferably as a dry powder or lyophilized form, comprising a filovirus entry inhibitor and preferably an appropriate diluent, which is combined with the dry or lyophilized composition shortly before administration as explained in the accompanying instructions of use. Pharmaceutical composition may also be packaged in single use pre-filled syringes or in cartridges for auto-injectors and needleless jet injectors. Multi-use packaging may require the addition of antimicrobial agents such as phenol, benzyl alcohol, meta-cresol, methyl paraben, propyl paraben, benzalconium chloride, and benzethonium chloride, at concentrations that will prevent the growth of bacteria, fungi, and the like, but that are non-toxic when administered to a patient.

Consistent with good manufacturing practices, which are in current use in the pharmaceutical industry and which are well known to the skilled practitioner, all components contacting or comprising a pharmaceutical composition must be sterile and periodically tested for sterility in accordance with industry norms. Methods for sterilization include ultrafiltration, autoclaving, dry and wet heating, exposure to gases such as ethylene oxide, exposure to liquids, such as oxidizing agents, including sodium hypochlorite (bleach), exposure to high energy electromagnetic radiation (e.g., ultraviolet light, x-rays, gamma rays, ionizing radiation). Choice of method of sterilization will be made by the skilled practitioner with the goal of effecting the most efficient sterilization that does not significantly alter a desired biological function of the filovirus entry inhibitor or other component of the composition.

Additional embodiments and features of the invention will be apparent from the following non-limiting examples.

Filoviruses

Filoviruses are enveloped, nonsegmented, negative-stranded (NNS) RNA viruses and constitute a distinct family within the order Mononegavirales. The family consists of the genera "Marburg-like" and "EBOV-like" viruses with the type species Marburg virus (MARV) and Ebola virus (EBOV), respectively. The genus of "EBOV-like" viruses is further subdivided into four distinct African (Ivory Coast, Sudan, Zaire, and Bundibugyo) and a single Asian (Reston) species.

Entry of EBOV into a host cell is mediated by a single viral glycoprotein (GP), a class I fusion protein. Therefore, interfering with the viral entry process is an attractive strategy for controlling virus infection. EBOV-GP consists of GP1 and GP2 subunits, which are linked by disulfide bonds and non-covalent interactions. GP1 is responsible for receptor binding and host tropism, while GP2 mediates viral/cell membrane fusion during viral entry.

Figure 1:
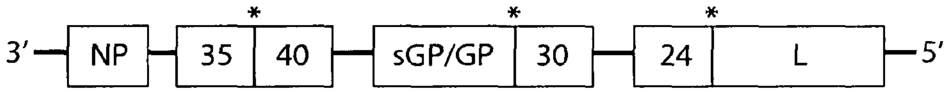
FIG. 1 is a schematic representation of the EBOV genome organization. The EBOV genome consists of a nonsegmented, negative-stranded (NNS) RNA molecule of approximately 19 kilobases. Genes are defined by highly conserved transcriptional start signals at their 3' ends and termination signals at their 5' ends, and are separated by intergenic regions varying in length and nucleotide composition. Some genes overlap, but the length of overlaps is limited to 5 highly conserved nucleotides (3'-UAAUU-5') within the transcriptional signals marked with asterisks "*".

The EBOV genome is about 19 kilobases. The viral genome contains seven genes, which direct the synthesis of eight viral proteins: envelope glycoprotein (GP), sGP, nucleoprotein (NP), VP24, VP30, VP35, VP40 and viral polymerase (L). See, FIG. 1. Sanchez, A., et al., (2001) op. cit. Genes are are delineated by conserved transcriptional signals, with a start site at the 3'-genome end, and terminating with a transcriptional stop (poly-adenylation) site (Volchkov, V. E., et al., *J. Gen. Virol.,* 80:355-362 (1999); Muhlberger, E., et al., *Virology,* 187:534-547 (1992); Muhlberger, E., et al., *Virology,* 223:376-380 (1996); Sanchez, A., et al., *Virus Res.,* 29:215-240 (1993); Calain, P., et al., *Virology,* 262:114-128 (1999)). The GP open reading frame of EBOV encodes two viral proteins (i) soluble 60- to 70-kDa (sGP) and (ii) full-length 150- to 170-kDa GP that inserts into the viral membrane through transcriptional editing (Sanchez, A., et al., *Proc. Natl. Acad. Sci. USA,* 93:3602-3607 (1996); Feldmann, H., et al., *Virus Res.,* 24:1-19 (1992); Feldmann, H., et al., *J. Gen. Virol.,* 82:2839-48 (2001); Volchkov, V. E., et al., *Virology,* 214:421-430 (1995)). Virus particles possess a central core, known as the ribonucleoprotein (RNP) complex that consists of NP, VP35, VP30, L and the viral RNA. The RNP complex is surrounded by a lipid envelope, with which the remaining proteins, GP, VP40 and VP24, are associated; these three proteins function as envelope glycoprotein, major matrix protein and minor matrix protein, respectively (Sanchez, A., et al. (2001), op. cit.). Finally, 3'-leader and 5'-trailer genomic components serve as encapsidation signals and replication and transcription promoters.

EBOV envelope glycoprotein (GP) is the sole envelope protein making up the virion surface spikes, which bind to the cellular receptor(s) and mediate viral entry (Feldmann, H., et al. (2001), op. cit.). The EboZ GP is synthesized in the endoplasmic reticulum (ER) as a 676 residue peptide (Sanchez, A., et al. (2001), op. cit.). A signal peptide of 32 residues at the N-terminus of GP is cleaved after translation. GP is further processed and modified during its transport through the ER and Golgi apparatus to the surface of the plasma membrane (Volchkov, V. E., et al., *Proc. Natl. Acad. Sci. USA,* 95:5762-7 (1998)). The N- and O-glycosylated GP0 (~160 kD) is cleaved by the host furin-like proteases in the Golgi apparatus, into two subunits, GP1 and GP2, which are linked by a single disulfide bond (Jeffers, S. A., et al., *J. Virol.,* 76:12463-72 (2002)). This cleavage, however, does not appear to be required for viral infection, at least in tissue culture (Wool-Lewis, R. J., et al., *J. Virol.,* 73:1419-26 (1999); Ito, H., et al., *J. Virol.,* 75:1576-80. (2001)). This is in stark contrast with other class I fusion proteins in which the cleavage of the glycoprotein is absolutely required for efficient viral infection (Skehel, J. J., et al., *Ann. Rev. Biochem.,* 69:531-69 (2000)). Like the influenza virus envelope protein hemagglutanin (HA), the native form of GP protein is composed of trimers of GP1-GP2 heterodimers (Sanchez, A., et al., *J. Virol.,* 72:6442-7 (1998)). The EboZ GP1, after cleavage of signal peptide, is 469 residues in length, with an apparent molecular weight of approximately 130 kD due to heavy N- and O-glycosylations. An important role of GP1 in viral infection is to specifically bind the cellular receptor(s) on the host cells. GP2 is 175 amino acids long and approximately 24 kD in size. The primary role of GP2 is to mediate viral/host membrane fusion and viral entry (Feldmann, H., et al. (2001), op. cit.). The sGP of EBOV shares approximately 300 residues with GP1, but has unique C-terminal 25 residues. Unlike GP, sGP forms homodimers that are linked in an antiparallel orientation by two disulfide bonds between the first and sixth cysteines on separate molecules (Sanchez, A., et al. (2001), op. cit.).

The x-ray core structure of the EBOV-GP has been reported (Lee, J., et al., *Nature,* 454:177-182 (2008); Malashkevich, V. N., et al., *Proc. Natl. Acad. Sci. USA,* 96:2662-7 (1999); Weissenhorn, W., et al., *Proc. Natl. Acad. Sci. USA,* 95:6032-6 (1998); Weissenhorn, W., et al., *Mol. Cell.* 2:605-16 (1998)). Three GP1 subunits assemble to form a chalice, cradled by the GP2 fusion subunits, while a novel glycan cap and projected mucin-like domain restrict access to the conserved receptor-binding site sequestered in the chalice bowl (Lee, J., et al., op. cit.). The glycocalyx surrounding GP is likely central to immune evasion and may explain why survivors have insignificant neutralizing antibody titers (Lee, J., et al., id.). The EBOV GP2 subunit shares several characteristic features with other viruses. EBOV GP2 is structurally similar to the transmembrane subunits of Rous sarcoma viruses (Gallaher, W. R., *Cell,* 85:477-478 (1996); Volchkov, V. E., et al., *FEBS Lett.,* 305:181-4 (1992)). The putative fusion peptide, which is thought to insert directly into the target membrane at an early stage in the membrane fusion stage, resides at the N-terminus. Following the fusion peptide is a region of heptad repeats which are implicated in formation of coiled-coil structures. Another predicted amphipathic helical region resides at the C-terminal end of the GP2 ectodomain. The C-terminal helices are packed in an antiparallel orientation into hydrophobic grooves on the surface of the coiled coil (6 helical bundle or hairpin), like that of HIV gp41 and SARS-CoV "S2". Mutational and functional analysis of the hydrophobic residues in the N— and C— helices indicated that some of these residues are important in mediating EBOV entry. Furthermore, it was shown that a peptide corresponding to the C-terminal helical region could inhibit GP pseudotyped VSV entry (Watanabe, S., et al. *J. Virol.,* 74:10194-201 (2000)).

In addition to its involvement in viral entry, GP has been implicated in filoviral pathogenesis by several groups. It has been demonstrated that overexpression of GP could lead to surface protein down-regulation and cell detachment, depending on cell type (Ray, R. B., et al., *Virology,* 321:181-188 (2004); Stroher, U., et al., *J. Virol.,* 75:11025-11033 (2001); Yang, Z. Y., et al., *Nat. Med.,* 6:886-889 (2000)). However, the direct role of GP in viral pathogenesis is still not clear. Recently it was shown that GP is shed as a result of proteolytic cleavage near the membrane region, and this shed GP can block virus-neutralizing antibodies (Volchkov, V. E., et al., *Science,* 291:1965-1969 (2001)).

EXAMPLE 1

Preparation of Pseudotype Viruses for Infection Inhibition Assays

Because of the biosafety concerns for EBOV and MARV, several efficient pseudotyping systems have been established to study EBOV and MARV entry in a BSL-2 laboratory. The EBOV pseudotype system typically utilizes either a recombinant vesicular stomatitis virus (VSV) or a retrovirus (HIV 1 or MuLV) core (Manicassamy, B., et al., *J. Virol.,* 79:4793-4805 (2005); Becker, S., et al., *J. Gen. Virol.,* 76:393-399 (1995); Chan, S. Y., et al., *Cell,* 106:117-126 (2001); Chandran, K., et al., op. cit.). Described herein is the generation of EBOV-GP (Zaire strain) pseudotyped viruses having either a HIV backbone with the luciferase reporter gene (HIV/EBOV-GP) or a VSV backbone (VSV/EBOV-GP) to mimic the EBOV-GP mediated entry process.

Briefly, HIV/EBOV-GP pseudotype viruses were generated by co-transfecting 293T cells with HIV vector envelope-defective proviral genome (pNL4.3.Luc.R-E-) containing a luciferase reporter (Muhlberger, E., et al., *Virology,* 223:376-380 (1996)) and EBOV-GP gene (Zaire strain) (GenBank accession number L11365).

The EBOV Zaire GP gene was synthesized by multiple rounds of overlapping PCR based on the EBOZ genome sequence (GenBank accession number L11365). Plasmid vectors expressing envelope protein of MARV (Lake Victoria strain) [MARV-G], vesicular stomatitis virus (VSV-G), lymphocytic choriomeningitis virus (LCMV) and Lassa virus (LASV), and Machupo (MACV) virus arenavirus were also used for comparative studies. See, Huang et al., *J. Biol. Chem.,* 281:3198-203 (2006); Lagging et al., *J. Virol.,* 72(5): 3539-46 (1998); Manicassamy B., et al., *J. Virol.,* 79:4793-4805 (2006).

Figure 2:
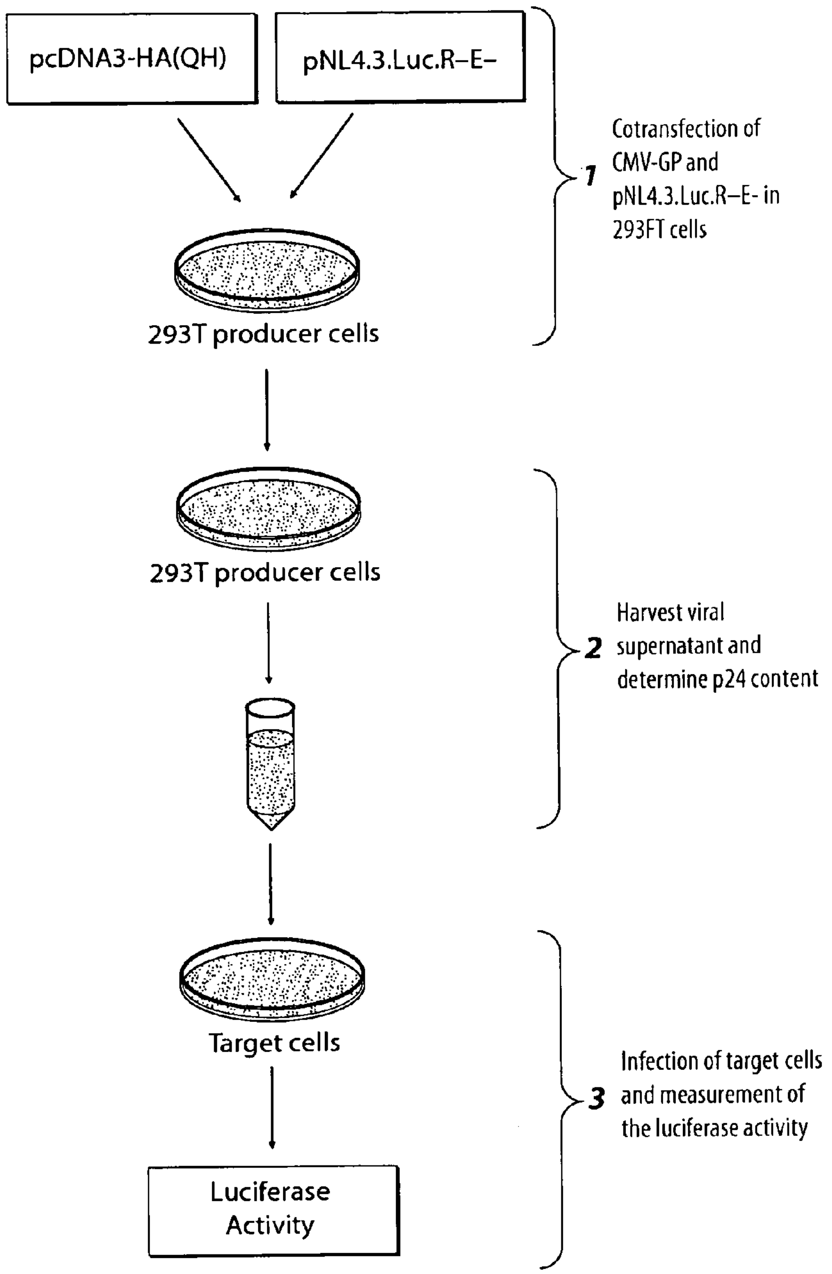
FIG. 2 is a workflow diagram describing HIV/EBOV-GP pseudotype virus production and infection. Ebola pseudotype viruses (HIV/EBOV-GP) were produced by co-transfecting 12 μg of wild-type (wt) or mutant EBOV-GP with 12 μg NL4-3-Luc-R-E-HIV vector into 293T cells (90% confluent) in 10 cm plates with Lipofectamine 2000 (Invitrogen) according to the supplier's protocol. The supernatants containing the pseudotype viruses were collected 48 hours post-transfection, pooled, clarified from floating cells and cells debris by low-speed centrifugation, and filtered through a 0.45 μm pore-size filter (Nalgene). The culture fluids were either used immediately or flash frozen in aliquots and stored at −80° C.

HIV/EBOV-GP pseudotype viruses (also referred to herein as "HIV/GP") were generated by co-transfection of 293T cells (8×$10^6$ cells in a 100 mm dish) with equal quantities (12 μg) of CMV-GP of EBOV Zaire Strain and the envelope-defective pNL4.3.Luc.R-E-HIV proviral genome (see, FIG. 2). Culture supernatants containing HIV/EBOV-GP viruses were collected ~24-48 hours post-transfection, clarified by centrifugation at 3,000×g for 15 min, and flash frozen into aliquots. HIV p24 antigen content was assessed using a commercially available EIA kit following manufacturer's instructions (Perkin-Elmer, Boston, Mass.). Virus infection was measured from the luciferase activity of the transduced cells and the time of incubation was optimized for maximum virus production. Background activity was determined as the luciferase activity of cells infected with supernatants transfected with empty pcDNA3.1 vector and the pNL4.3.Luc.R-E-. Pseudotype virus expressing the envelope glycoprotein of VSV (HIV/VSV-G) used as a control in the experiments below, was generated as described for HIV/EBOV-GP.

To confirm the specificity of HIV/EBOV-GP pseudotype virus, it was first determined whether the HIV/EBOV-GP could be neutralized by a GP-specific human monoclonal antibody (KZ52) and by serum from guinea pig immunized with the EBOV-GP both of which have been previously shown to neutralize infectious EBOV. The human monoclonal antibody was a gift from Dr. Denis Burton at Scripps Research Institute (Parren, P. W., et al., *J. Virol.,* 76:6408-12 (2002)); the guinea pig serum was a gift from Dr. Sina Bavari, at USAMRIID. HIV/VSV-G was used as a control. All antibodies were incubated with HIV/EBOV-GP or HIV/VSV-G for 1 hour at 37° C., and the 293T cells were infected with the virus/antibody mixtures. The human monoclonal antibody (KZ52) and anti-EBOV-GP guinea pig serum displayed a dose-dependent neutralization of HIV/EBOV-GP, neutralizing greater than 75% of the HIV/EBOV-GP virus out to a 1/400 dilution. In contrast, even at only 1/50 dilution, the human monoclonal antibody and guinea pig antiserum failed, only neutralizing about 25% of the control HIV/VSV-G virus. These results confirm that HIV/EBOV-GP in 293T cells mimics the EBOV-GP-mediated infection process. The specificity of the VSV/EBOV-GP virus was also confirmed using the same antibodies (Table 1).

TABLE 1

Infectivity of 293FT cells by pseudotype viruses

| pseudotype virus[a] | antibodies tested[b] | PFU/ml |
|---|---|---|
| VSV/EBOV-GP | none (control) | $4.83 \times 10^6$ |
| | human anti-EBOV-GP monoclonal | 100 |
| | guinea pig anti-EBOV-GP serum | 25 |
| | rabbit anti-VSV-G serum | $2.89 \times 10^6$ |
| VSV/VSV-G | none (control) | $6.5 \times 10^8$ |
| | human anti-EBOV-GP monoclonal | $5.5 \times 10^8$ |
| | guinea pig anti-EBOV-GP serum | $3 \times 10^8$ |
| | rabbit anti-VSV-G serum | $6.5 \times 10^3$ |

[a]pseudotype viruses were generated by infection of stable BHK cells expressing EBOV Δ mucin GP with VSV ts045.
[b]rabbit polyclonal and guinea pig antisera were tested at 1/25 dilution.
Virus titers are mean of three experiments.

The endosomal protease cathepsin B (CatB) is essential for entry of EBOV into cells (Chandran, K., et al., op. cit.; Schornberg, K., et al., *J. Virol.* 80:4174-8 (2006)). The potential EBOV infection specificity of the HIV/EBOV-GP pseudotype virus was further validated by using a CatB specific inhibitor CA-074 (Chandran, K., et al., op. cit., Schornberg, K., et al., op. cit.). 293T cells (8×$10^3$ cells/well, plated 24 hours before infection in a 96 well plate) were preincubated with 5 μM CA-074 at 37° C. for 3 hours. 100 μL of HIV/EBOV-GP virus containing 4 μg/mL polybrene and CA-074 at 10 μM were added in each well. The medium was replaced after 5 hours incubation and following 72 hours incubation, luciferase activity was measured. As a negative control, CA-074 treated cells were similarly infected with HIV/VSV-G. The specific CatB inhibitor CA-074 strongly inhibited HIV/EBOV-GP infection but not HIV/VSV-G infectivity. Similar results were also obtained utilizing a VSV/EBOV-GP pseudotype virus. These results further demonstrate the validity of HIV/EBOV-GP pseudotype virus as a surrogate model for infectious wt EBOV binding and entry.

EXAMPLE 2

Selection of Virus and Cells for High Throughput Screening (HTS)

The HIV/EBOV-GP and the VSV/EBOV-GP pseudotype viruses engineered in Example 1 were evaluated for HTS suitability. The HIV/EBOV-GP pseudotype virus with the luciferase reporter gene was chosen for the final HTS screen because of its sensitivity and reproducibility in a 96 well plate format (data not shown).

To further develop the HTS assay, the infectivity of the HIV/EBOV-GP pseudotype virus was investigated in different cell lines. Vero, 293T, HeLa, HepG2 and BHK cells were chosen as suitable HIV/EBOV-GP target cell lines (Wool-Lewis, R. J., et al., op. cit.; Watanabe, S., et al., op. cit.; Manicassamy, B., et al. op. cit.; Becker, S., et al. op. cit.; Chan, S. Y., et al., op. cit.; Chandran, K., et al., id.; Schornberg, K., et al., op. cit.). As shown in FIG. 3, the maximum activity to background ratio was obtained with 293T cells. Precision statistical parameters including signal to background ratio (S/B), and the screening window coefficient Z factor (Z') were calculated according to Zhang's method (Zhang, J. H., et al., *J. Biomol. Screen,* 4:67-73 (1999)). Z' is defined as the ratio of separation band to the signal dynamic range of the assay. The Z' takes into account the assay signal dynamic range, data variation associated with sample measurement and data variation associated with reference control measurements. Z' provides a useful tool for comparison and evaluation of the robustness of HTS assays and can be utilized in assay optimization and validation. The S/B value and Z' factor were calculated for each assay plate.

For an assay to qualify as robust, the S/B value should be ≥10 and Z'>0.5. Z' values, were consistently positive (Z'>0.5) in the HIV/EBOV-GP infectivity assay utilizing 293T cells (data not shown), confirming the overall suitability for HTS. The standard variation of the relative luciferase unit (RLU) value among the positive controls was >25% in the 293T assay. Therefore, 293T cells were chosen for the HTS.

EXAMPLE 3

Screening a Diverse Compound Library to Identify/Confirm Selective EBOV Inhibitors The HIV/EBOV-GP pseudotype virus HTS was performed in human 239T cells at a compound concentration of 25 μM. A workflow diagram describing criteria for isolation of inhibitors from the HTS screen is shown in FIG. 4. An inhibition of >90% ($IC_{90}$) of luciferase activity was designated as a "primary hit". Controls were included on each plate: 2 blank wells for background correction, 8 wells for 0% inhibition (DMSO only, no test compound=negative control) and 6 wells with no infection. A chemical library of 52,500 diverse small molecular weight compounds was screened. Compounds were in the molecular weight range of 200-500 Da, and obtained from several vendors: Chembridge (San Diego, Calif.), Timtec (Newark, Del.), and ChemDiv (San Diego, Calif.). The compounds in the libraries were pre-selected using numerous "drug-like" chemical filters, including Lipinski's 'Rule of 5' (Lipinski, C. A., et al., *Adv. Drug. Deliv. Rev.,* 46: 3-26 (2001)), i.e., low molecular weight (≤500 Da), cLogP (≤5.0), numbers of H-bond donors (≤5), and H-bond acceptors (≤10), to remove undesirable compounds. Known cytotoxic scaffolds, such as metal complexes, highly conjugated ring systems, oxime esters, nitroso and strong Michael acceptors were also removed.

Screening of combinatorial chemical libraries using the HIV/EBOV-GP pseudotype virus was performed in 96 well plates. The final concentration of test compound was 25 μM while the final concentration of DMSO in all wells was maintained at 1%. Low passage 293T cell monolayers were infected with 100 μL of p24 normalized HIV/EBOV-GP pseudotype virus containing 8 μg/ml polybrene in the presence of test compounds. After 5 hours, the inoculum was removed, the cells were washed briefly and then incubated for 72 hours. Prior to each screening, each batch of the viral preparation was titrated to determine the amount of virus required to infect the target cells, so that a relatively high luciferase activity could be recorded while still remaining in a linear response range ($10^5$-$10^6$ RLU). Infection was quantified using the Britelite Plus™ assay system (Perkin Elmer, MA) in a Wallac EnVision 2102 Multilabel Reader (Perkin Elmer, MA). Test compounds were in DMSO solutions with 80 compounds per plate. Controls were also included in each plate; 8 wells for 0% inhibition (DMSO only, maximum signal=positive control) and 8 wells for 100% inhibition (e.g., known EBOV inhibitor E-64, minimum signal=negative control). The percent inhibition was calculated as:

$$\frac{[RLU^{*}\text{ in the presence of compound}] - [RLU\text{ of negative control}]}{[RLU\text{ of positive control}] - [RLU\text{ of negative control}]} \times 100\%$$

$$*RLU = \text{relative luciferase units}$$

A total of 1,146 compounds (2.2%) were found to inhibit HIV/EBOV-GP pseudotype virus at a 25 μM screening concentration (see, Table 2). These compounds were designated as "primary hits". The screening window coefficient (Z' factor), a precision statistical parameter, was calculated according to Zhang's method (Zhang et al 1995) and results from assays with Z' factor values between 1 and 0.5 (1>Z'≥0.5) were considered.

After HIV/EBOV-GP pseudotypes enter the target cell, viral RNA is reverse transcribed, actively imported into the nucleus, and stably integrated into the genome. Therefore, in addition to entry inhibitors, the "primary hits" might also include non-specific inhibitors of transcription and translation along with inhibitors of the reporter luciferase gene. The 1,146 primary hits were tested against HIV/VSV-G pseudotypes, as a counter screen, to eliminate those compounds not specifically acting as HIV/EBOV-GP entry inhibitors.

TABLE 2

Results of the screening of compound libraries

| Compounds Screened | Number of: primary hits (inhibition of HIV/ EBOV-GP in the HTS screen) [%][a] | Primary hits inhibiting HIV/ VSV-G [%][a,b] | Specific hits (Primary hits inhibiting HIV/ EBOV-GP only) [%] | Specific Hits displaying CC50 > 25 μM[c] |
|---|---|---|---|---|
| 52,500 | 1,146 [2.2] | 1,089 [2.07] | 57 [0.13] | 18 |

[a]HIV/EBOV-GP and HIV/VSV-G were generated by transfection of 293T cells with pNL4.3.Luc.R-E- as the HIV-1 expression vector and with EBOV-GP or VSV-G respectively.

[b]1,089 primary hits inhibited HIV/VSV-G by more than 90% at 25 μM whereas the RLU values of the controls varied by >20%

[c]$CC_{50}$ was determined using "CellTiter 96 aqueous non-radioactive cell proliferation assay" (Promega, Madison, WI)

Both the HIV/VSV-G used as a counter screen and the HIV/EBOV-GP used in the HTS have the identical HIV backbone, but express different envelop proteins, VSV-G and EBOV-GP, respectively. The screening of the "primary hits" against HIV/VSV-G was done in a similar fashion as described with the HIV/EBOV-GP pseudotype. In the counter screen, a total of 1,089 of the 1,146 compounds were found to also inhibit HIV/VSV-G infection by more than 90% at a 25 μM concentration (see, Table 2 and FIG. 4). These non-specific inhibitors were discarded.

Cell death could also result in a decrease in luciferase activity. Therefore, the 57 primary hits were evaluated for cytotoxicity against 293T cells using the "CellTiter 96 aqueous non-radioactive cell proliferation assay" (Promega, Madison, Wis.). Eighteen of the 57 primary hits were found to have $CC_{50}$ values >25 μM. These 18 compounds were then either synthesized or re-ordered, from different batches from the original vendors, and re-tested. All 18 compounds were found to re-confirm activity against the HIV/EBOV-G pseudotype virus compared to the original sample (data not shown). Dose response curves were generated for these 18 compounds and their $IC_{90}$ values were determined as shown in Table 3.

TABLE 3

Dose response curves for the 18 selected hit compounds

| | Inhibition of pseudotype virus at 25 μM in 293T cells (%)[a] | | $IC_{90}$ (μM) against |
|---|---|---|---|
| Compound# | HIV/EBOV-GP | HIV/VSV-GP[b] | HIV/EBOV-GP[c] |
| 1 | 98 | 25 | 18.4 |
| 2 | 100 | 10 | 7.6 |
| 3 | 98 | 0 | 0.8 |
| 4 | 100 | 15 | 1.1 |
| 5 | 98 | 25 | 20.8 |
| 6 | 98 | 20 | 10.9 |
| 7 | 96 | 20 | 20.1 |
| 8 | 100 | 30 | 23.5 |
| 9 | 100 | 25 | 1.5 |
| 10 | 92 | 25 | 11.5 |
| 11 | 95 | 10 | 10.5 |
| 12 | 100 | 5 | 15.8 |
| 13 | 100 | 25 | 12.3 |
| 14 | 93 | 30 | 19.5 |
| 15 | 100 | 22 | 15.2 |
| 16 | 95 | 20 | 13.5 |
| 17 | 96 | 15 | 12.6 |
| 18 | 97 | 10 | 11.5 |

[a]HIV/EBOV-GP and HIV/VSV-G were generated by transfection ot 293T cells with pNL4.3.Luc.R-E- as the HIV-1 expression vector and with EBOV-GP or VSV-G respectively.
[b]Compounds passed the HIV/VSV-G counter screen if they displayed <30% inhibition which is the variation observed in the positive control
[c]$IC_{90}$ was determined using synthesized or re-ordered compounds as different batches from the original vendors

EXAMPLE 4

EBOV Inhibitor Confirmation Against Infectious EBOV

The anti-EBOV activity of the eighteen "specific hit" compounds from Example 3 were tested against infectious EBOV (Zaire subtype, 1995 strain) in a biosafety level 4 containment facility at USAMRIID, Fredrick, Md.

A cell culture grown recombinant Zaire EBOV expressing green fluorescent protein (GFP-ZEBOV) as a reporter for virus replication was used to screen compounds for inhibition of EBOV replication using methods described in Aman et al., *Antiviral Res.,* 83:245-51 (2009) (see also Panchal et al, *Cell Host Microbe.,* 6:162-73 (2009). Briefly, Vero E6 cells (40×$10^3$ cells/well in a 96-well plate format) were infected with the recombinant GFP-ZEBOV at a multiplicity of infection of 5 in presence of the compounds. Cultures were incubated for 48 hours before fixation (10% neutral-buffered formalin, 72 hours) and removal from the BSL4 facility. After nuclear (Hoechst dye) and cytoplasm/nuclear staining (HCS cell mask deep red stain), viral infection was imaged and quantified using an automated Opera confocal reader (Model 3842-Quadruple Excitation High Sensitivity (QEHS), Perkin-Elmer, Waltham, Mass.). Images were analyzed within the Opera environment using standard Acapella scripts. This procedure identifies the total number of adherent cells, and fraction of infected cells, thereby providing an immediate assessment of efficacy and toxicity. Cell viability assays were conducted using the method described in Warren et al., Antiviral activity of a small-molecule inhibitor of filovirus infection, *Antimicrob. Agents Chemother.,* 54:2152-9 (2010).
All assays were repeated at least three times. Percent inhibition values were calculated as follows:

$$1 - \frac{\text{average } GFP \text{ fluorescence from compound-treated wells}}{\text{average fluorescence from wells containing medium only}} \times 100\%$$

Full dose-response curves were generated for each of the 18 specific hit candidates. In parallel, assays were employed to determine compound-induced cytotoxicity in the absence of virus infection. As shown in Table 4, below, of the original 18 hit candidates from Example 3, eight compounds were found to inhibit the infectious recombinant EBOV with $IC_{50}$ values <20 μM.

TABLE 4

Activity of the confirmed hit compounds against pseudotype and infectious EBOV

| | | HIV/EBOV-Gp | | | GFP-ZEBOV | | | |
|---|---|---|---|---|---|---|---|---|
| Compound | Structure | $IC_{90}$ (μM)[a] | $CC_{50}$ (μM)[b] | SI[c] | $IC_{50}$ (μM)[d] | $IC_{90}$ (μM)[d] | $CC_{50}$ (μM)[e] | SI[c] |
| A | 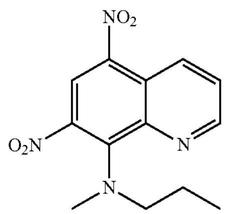 [SMILES: CCCN(C)c1c([N+](=O)[O-])cc([N+](=O)[O-])c2cccnc12] | 18.4 | 30 | 1.6 | 7.5 | 10 | 15 | 2 |

TABLE 4-continued
Activity of the confirmed hit compounds against pseudotype and infectious EBOV
| Compound | Structure | HIV/EBOV-Gp IC$_{90}$ (μM)[a] | HIV/EBOV-Gp CC$_{50}$ (μM)[b] | HIV/EBOV-Gp SI[c] | GFP-ZEBOV IC$_{50}$ (μM)[d] | GFP-ZEBOV IC$_{90}$ (μM)[d] | GFP-ZEBOV CC$_{50}$ (μM)[e] | GFP-ZEBOV SI[c] |
|---|---|---|---|---|---|---|---|---|
| B | 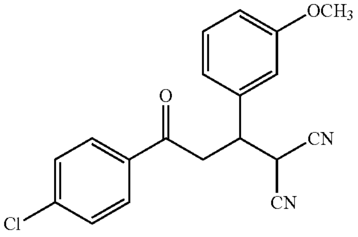 [SMILES: COc1cccc(C(CC(=O)c2ccc(Cl)cc2)C(C#N)C#N)c1] | 7.6 | 25 | 3.28 | 10 | 20 | 51.5 | 5.15 |
| C | 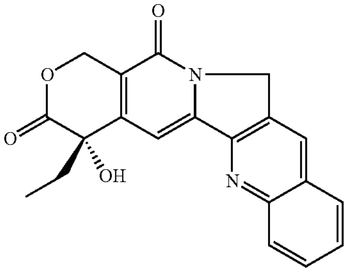 [SMILES: CC[C@@]1(O)C(=O)OCc2c1cc1n(c2=O)Cc2cc3ccccc3nc2-1] | 0.8 | 20 | 25 | 10 | 23.5 | 29.5 | 2.95 |
| D | 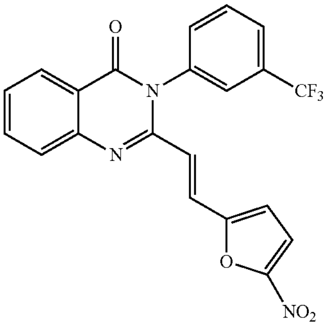 [SMILES: O=c1c2ccccc2nc(/C=C/c2ccc([N+](=O)[O-])o2)n1-c1cccc(C(F)(F)F)c1] | 1.1 | 30 | 27.2 | 15.5 | >25 (85%) | 62.5 | 4.03 |
| E | 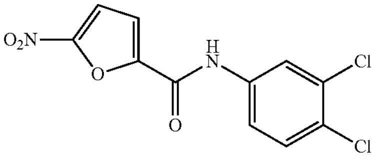 [SMILES: O=C(Nc1ccc(Cl)c(Cl)c1)c1ccc([N+](=O)[O-])o1] | 20.8 | 54 | 2.59 | 14.5 | 20 | 40 | 2.75 |
| F | 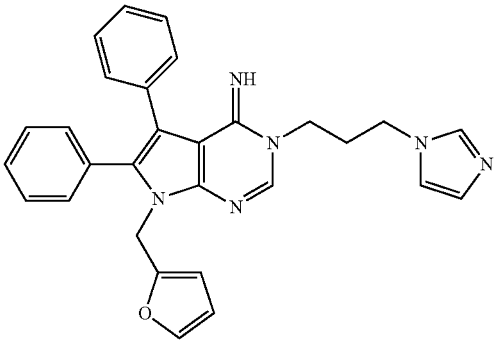 [SMILES: N=c1c2c(-c3ccccc3)c(-c3ccccc3)n(Cc3ccco3)c2ncn1CCCn1ccnc1] | 10.9 | 25 | 2.2 | 15 | >25 (78%) | 48.5 | 3.2 |

TABLE 4-continued

Activity of the confirmed hit compounds against pseudotype and infectious EBOV

| | | HIV/EBOV-Gp | | | GFP-ZEBOV | | | |
|---|---|---|---|---|---|---|---|---|
| Compound | Structure | $IC_{90}$ (μM)[a] | $CC_{50}$ (μM)[b] | SI[c] | $IC_{50}$ (μM)[d] | $IC_{90}$ (μM)[d] | $CC_{50}$ (μM)[e] | SI[c] |
| G | 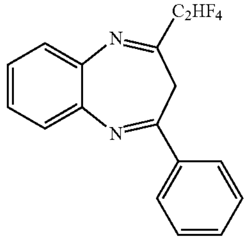 | 12.1 | 75 | 6.19 | 10 | >25 (70%) | 55.2 | 5.5 |
| H | 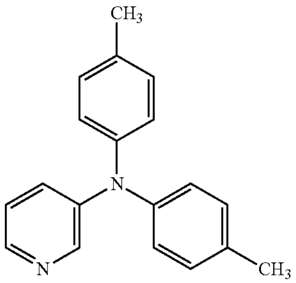 [SMILES: Cc1ccc(N(c2ccc(C)cc2)c2cccnc2)cc1] | 23.5 | >50 | 2.12 | 20 | >25 (59%) | 22.6 | 1.1 |

[a]HIV/EBOV-GP was generated by transfection of 293T cells with pNL4.3.Luc.R—E— as the HIV-1 expression vector and with EBOV-GP. $IC_{90}$ values were determined using either synthesized or re-ordered compounds as different batches from the original vendors.
[b]293T cells were treated with compound alone. $CC_{50}$ values were determined from linear portions of the dose response curve.
[c]selectivity index (SI) = $CC_{50}/IC_{50}$.
[d]All experiments with GFP-ZEBOV were performed under biosafety level 4 conditions. GFP-ZEBOV was incubated with Vero E6 cells at a multiplicity of infection of 1 for 1 hour in the presence or absence of inhibitor compounds. Virus was removed after 1 hour, cells were washed in PBS, incubated for 48 hours, and percentage of GFP-expressing cells was measured. $IC_{50}$ and $IC_{90}$ values were determined from the linear portion of the full dose response curve.
[e]Vero E6cells were treated with compound alone. $CC_{50}$ values were determined from linear portions of the dose response curve.

Three of these compounds exhibited $CC_{50}$ values >50 μM, indicating low cytotoxicity (i.e., higher concentration to reach 50% cell toxicity). The dose response curves for these three compounds (B, D, and G) are shown in FIG. 5. Two of these compounds (B, G) have an in vitro selectivity index (SI) >5. The overall true-hit identification rate of screening for EBOV-GP mediated entry process was ~0.015%. The $IC_{50}$ values of these 8 confirmed hit compounds are approximately one log higher in the recombinant GFP-EBOV assay than in the HIV/EBOV-GP pseudotype assay (see, Tables 3 and 4). This may be due to the expected higher density of EBOV GP on the surface of the infectious virus.

EXAMPLE 5

Mechanism of Action (MOA) and Filovirus Inhibitory Spectrum

The eight confirmed EBOV inhibitors from Example 4 were further investigated to determine whether they also inhibit Marburg virus (MARV) using a pseudotype MARV also having a HIV backbone. MARV is also a member of the filovirus family and causes hemorrhagic fever in humans and non-human primates. MARV pseudotype virus bearing MARV GP (HIV/MARV-GP) was generated in a similar fashion as the HIV/EBOV-GP pseudotypes in Example 1. Although both the viruses are closely related, their infection efficiencies in different cell lines or following glycosidase or protease treatment have led to the suggestion that these viruses utilize distinct host receptors or entry mechanisms (Chan, S. Y., et al., *J. Virol.* 74: 4933-4937 (2000)). All of the confirmed inhibitors A-H displayed significant activity against HIV/MARV-GP pseudotype virus (see, FIG. 6). The results suggest that the viral entry inhibitor compounds A through H confirmed as EBOV inhibitors also have activity against other human pathogenic filoviruses, such as MARV.

EXAMPLE 6

Cell Surface Blocking Analysis

The filovirus inhibitor compounds A-H can inhibit EBOV entry by either inhibiting the binding of the virus with its receptor or inhibiting the fusion process. A series of cell surface blocking analysis experiments was performed with the HIV/EBOV-GP pseudotype virus to determine the ability of the eight inhibitors of Example 4 to bind with host cell surface receptors and/or viral GP to block viral entry into the cells. The virus or virus-compound (10 μM) mixture was first added to 293T cells (~80% confluent and plated overnight) and incubated at 37° C. for 2 hours. The cells were washed, fresh medium with or without compound was added, and cells incubated for an additional 72 hours. As shown in FIG. 7 (Assay 1), six of the confirmed hits displayed >75% inhibition in viral activity when added only during the virus infection phase of the assay. However, the compounds exhibited much less inhibitory activity (<30%) when added after the infection phase of the assay (see, FIG. 7, Assay 2). This residual activity is similar to their cytotoxicity values (data not shown).

Next it was explored whether the inhibitors were acting as "attachment inhibitors" by binding with EBOV-GP, or as "receptor antagonists" by binding to the host surface receptors and blocking interaction with EBOV-GP. Predetermined titers of HIV/EBOV-GP pseudotype virus were treated with the compounds A-H from Example 4 at 10 μM for 1 hour at 37° C. Following incubation, the virus-compound mixture was added to 293T cells (~80% confluent and plated overnight), and incubated at 37° C. for 2 hours. The cells were washed, fresh medium was added and cells incubated for an additional 72 hours. Untreated virus was used as a positive control. As shown in FIG. 7 (Assay 3), under these conditions the inhibitor compounds B and C displayed an inhibition of HIV/EBOV-GP infection >75%. At the 37° C. incubation temperature normal recycling of the host membrane receptors will occur. Therefore, coupled with the results described above, these data suggest that inhibition with compounds B and C may be due to the binding of the inhibitor with EBOV-GP, preventing attachment of the virus to cell surface receptors.

"Receptor antagonists" bind to the host surface receptors, and prevent EBOV-GP-mediated binding to host cells. To determine whether the inhibitors A-H in Example 4 are acting as "receptor antagonists", 293T cells were cooled to 4° C., the eight confirmed hits were then added to wells at a 10 μM concentration in ice cold Dulbecco's modified Eagle's medium (DMEM), and cells incubated for 60 min on ice. The incubation at low temperature reduces receptor-mediated uptake of the compounds by the cells. After 60 minutes, unbound compounds were removed by washing. A predetermined titer of HIV/EBOV-GP was added to each well, and incubated at 4° C. for 1 hour. Unbound viruses from each well were removed by rinsing three times with ice-cold DMEM and fresh medium was added. Cells were then further incubated at 37° C. for 72 hours. Viral inhibitor compounds D and F displayed inhibition of infection >75% in this assay (see, FIG. 7, Assay 4), suggesting that they may be binding to the cellular receptors and thereby inhibiting EBOV entry (see, FIG. 7). See also, data for compounds B, D, and G in FIG. 8.

EXAMPLE 7

The Inhibitor Compounds do not Block Fusion of Virus with Host Cells

A viral inhibitor might block viral entry by inhibiting the virus/host cell fusion process. To investigate whether the inhibitors of the invention were inhibiting cell fusion, a novel cell-cell fusion assay was used, as developed by Takikawa et al. (Takikawa, S., et al., *J. Virol.,* 74:5066-5074 (2000)), that quantitatively measures the fusogenic activity of recombinant glycoproteins of enveloped viruses.

Two distinct cell lines were used: one was 293T cell lines expressing EBOV Δmucin GP on the cell surface and T7 RNA polymerase in its cytoplasm; the other was a Vero cell population containing a luciferase gene linked to a T7 promoter. 293T cells ($8\times10^5$ cells in a 35-mm-diameter plate) were transfected with either a EBOV Δmucin-GP or a VSV-G expressing plasmid (0.25 μg), together with reporter plasmids, pDNA3-Luc (1.0 μg) using Lipofectamine 2000. pcDNA3-Luc plasmid has a firefly luciferase gene under the control of the T7 promoter. The Vero E6 cells ($2\times10^5$ cells per well in a 24-well plate) were infected with vaccinia virus expressing T7 RNA polymerase (VVT7) at MOI of 1 and incubated for 12 hours. 48 hours after transfection, the 293T cells were treated with 0.05% EDTA in PBS and suspended in DMEM containing 10% FBS. The 293T cells ($2\times10^5$ cells per well) were overlaid onto the target Vero cells and incubated for 5 hours. The co-cultured cells were bathed in PBS at pH 5.0 for 2 minutes at 37° C. in presence or absence of the eight inhibitor compounds A-H and then were incubated with DMEM containing 10% FBS for 5 hours. The cell fusion activity was quantitatively determined by measuring luciferase activity from the lysates of the cocultured cells. Cells expressing EBOV Δmucin GP exhibited a low level of activity compared to the cells expressing the VSV-G protein. None of the compounds A-H prevented the fusion process, whereas the control compound Bafilomycin at 10 μM completely inhibited fusion of VSV-G and EBOV expressing cells.

EXAMPLE 8

The Inhibitor Compounds do not Inhibit Cathepsin B and L Activity

Recently, two groups have independently demonstrated that human cathepsin B (CatB) and cathepsin L (CatL) mediate EBOV entry into the cells by proteolysis of the EBOV GP1 subunit (see, Chandran, K., et al., op. cit.; Schornberg, K., et al., op. cit.). Proteolysis of the GP1 subunit exposes the GP2 fusion domain resulting in entry of EBOV into the cells. Compounds A-H were tested on CatB and CatL using a fluorometric assay that contains an internally quenched fluorogenic peptide Z-Phe-Arg-AMC as substrate.

Recombinant CatL and CatB were purchased from Calbiochem (North American affiliate of Merck KGaA, Darmstadt, Germany). The inhibitor compounds were serially diluted to 1 μM, 10 μM, and 100 μM and were pre-incubated with CatB and CatL for 1 hour. Following incubation, the fluorogenic peptide substrate, Z-Phe-Arg-AMC was added to the cells and incubated for 1 hour at 37° C. Cleavage of the substrate by Cat B or CatL releases AMC and the fluorescence can be measured at 360 nm excitation and 460 nm emission. The compounds A-H did not interfere with cathepsin-mediated viral entry at any of the test concentrations, indicating that none of the isolated inhibitors A-H act at this stage of the EBOV entry process.

EXAMPLE 9

Supplemental Screening of a Diverse Compound Library for Additional Inhibitors

In view of the successful determination and characterization of the eight confirmed filovirus inhibitor compounds in the foregoing examples, a supplemental HTS was performed utilizing a chemically diverse, random library of an additional 50,000 compounds.

The supplemental HTS was performed in the same manner as Example 3, above, following the screening plan depicted in FIG. 4. Thirty-three of the initial 1,562 primary hit compounds successfully passed through the secondary counter assay and cytoxicity assay.

EXAMPLE 10

EBOV Inhibitor Confirmation Against Infectious EBOV

The anti-EBOV activity of the thirty-three "specific hit" compounds from Example 9 were tested against infectious EBOV (Zaire subtype, 1995 strain) in a biosafety level 4 containment facility at USAMRIID, Fredrick, Md. following the procedure described in Example 4, except that an $IC_{50}$ of less than 25 μM (as compared with <20 μM) was used as the cut-off. Of the original thirty-three hit candidates from Example 9, nineteen compounds were found to inhibit the infectious recombinant EBOV with $IC_{50}$ values <25 μM. These included clusters of multiple chemically related structures, as well as singletons.

Table 5 shows four representative confirmed hits with the best activity against infectious EBOV, the least cytotoxicity (i.e., SI>5) and suitable "drug-like" features for medicinal chemistry optimization. Compound G is a representative confirmed hit from Examples 4-8. Compounds I, J, and K are new confirmed hits, identified from the supplemental screening of an additional 50,000 compounds from Examples 9-10, with superior SI's (SI=9-20) than the original hit series of compounds. Compounds I and J are structurally related amino-acetamide sulfonamides.

TABLE 5

Potency and Selectivity of representative confirmed hits

| Cpd | Structure | HIV/EBOV-GP $IC_{90}$ (μM)[a] | HIV/EBOV-GP $CC_{50}$ (μM)[b] | HIV/EBOV-GP SI[c] | Infectious EBOV $IC_{50}$ (μM) | Infectious EBOV $CC_{50}$ (μM)[b] | Infectious EBOV SI[c] | HIV/MARV-GP $IC_{90}$ (μM)[a] | HIV/LASV-GP $IC_{90}$ (μM)[a] | HIV/HA (H5) $IC_{90}$ (μM)[a] |
|---|---|---|---|---|---|---|---|---|---|---|
| G | 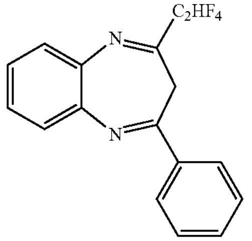 | 12.1 | 75 | 6 | 10 | 55 | 6 | 10 | >50 | >50 |
| I | 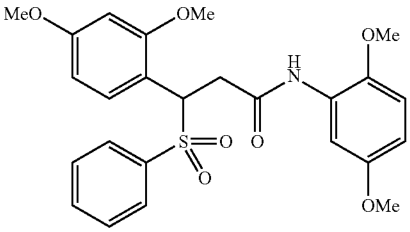 [SMILES: COc1ccc(OC)c(NC(=O)CC(c2ccc(OC)cc2OC)S(=O)(=O)c2ccccc2)c1] | 2.7 | 32 | 12 | 4.6 | 40 | 9 | 2.8 | >50 | >50 |
| J | 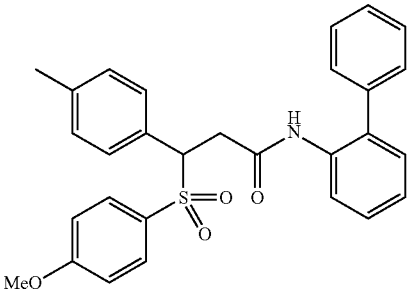 [SMILES: COc1ccc(S(=O)(=O)C(CC(=O)Nc2ccccc2-c2ccccc2)c2ccc(C)cc2)cc1] | 0.8 | 80 | 100 | 4.8 | 85 | 18 | 4.6 | >50 | >50 |
| K | 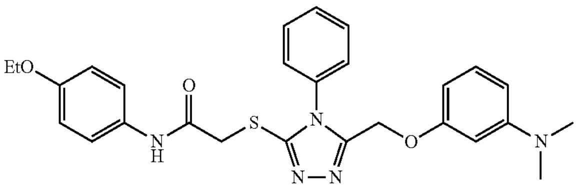 [SMILES: CCOc1ccc(NC(=O)CSc2nnc(COc3cccc(N(C)C)c3)n2-c2ccccc2)cc1] | 2.0 | 98 | 98 | 2.5 | 50 | 20 | 11 | >50 | >50 |

[a]Pseudotype virus was generated by co-transfection of 293T cells with pNL4.3.Luc.R—E— and respective envelop glycoprotein. $IC_{90}$ was determined using synthesized or re-ordered compounds as different batches from the original vendors.

[b]$CC_{50}$ values were determined from linear portions of the dose response curve

[c]selectivity index (SI) = $CC_{50}/IC_{50}$

EXAMPLE 11

Filovirus Inhibitory Spectrum of the Confirmed Hit Compounds

The nineteen confirmed hits from Example 10 were further investigated to determine whether they also inhibit MARV filoviruses using pseudotype MARV also having a HIV backbone. All of the 19 confirmed anti-EBOV hits displayed significant activity against HIV/MARV-GP pseudotypes ($IC_{50}$ values <25 μM; Table 5). The results suggest that the 19 additional confirmed inhibitors have broader activity against human pathogenic filoviruses.

The critical amino acid residues important for virus entry in the envelope glycoprotein are conserved between the MARV and EBOV viruses (Kuhn, J. A., et al., op. cit.; Manicassamy, B., et al., op. cit.), and the results of this example and Example 5 suggest the compounds may be binding in the conserved region.

The specificity of all confirmed hits was further evaluated by assays against a number of other viruses bearing type 1 envelope proteins using both pseudotype viruses and infectious viruses. Pseudotype viruses bearing the envelope protein of Lassa virus (LASV) [HIV/LASV-GP] and bearing the hemagglutinin (HA) envelope protein of influenza virus subtype H5 [HIV/HA(H5)] were generated using the same HIV backbone (see, Example 1). Representative data for these assays appear in Table 5 for the compounds G, I, J, and K. None of the inhibitor compounds tested inhibited HIV/LASV-GP or HIV/HA(H5), indicating specificity of the inhibitors for filoviruses.

EXAMPLE 12

Time of Addition Study

EBOV entry is a multistep process that can broadly be divided into two major steps: (1) virus attachment and receptor binding, followed by (2) receptor-mediated endocytosis, pH-dependent GP processing and membrane fusion. To supplement the data obtained in Examples 6-7, a time-of-addition experiment was performed with HIV/EBOV-GP. Compounds were added 1 hour before infection (−1 h), during infection (0 h) and 1 hour postinfection (+1 h) as shown in FIG. 9. Controls consisted of DMSO (negative control) and E-64 (positive control), a pan-caspase inhibitor that inhibits EBOV infection (Chandran, K., et al., op. cit.). All of the compounds tested, when added during the virus adsorption process (at 37° C.), inhibited more than 75% of HIV/EBOV-GP infection (see, FIG. 9, "entry"). Compound G was also active (>75% inhibition) when added at time 0 at 0° C. (see, FIG. 9, "binding"), but not at −1 hr or +1 hr, suggesting possible interference with virus binding. In contrast, the aminoacetamide sulfonamide series compounds I and J, were active when added after (+1 h) virus infection (see, FIG. 9, "fusion"), but not at −1 hr or 0 hr, suggesting possible interference with the fusion process.

EXAMPLE 13

Structure-Activity Relationship (SAR) Evaluation

In view of the foregoing results, a preliminary SAR evaluation of confirmed filovirus inhibitors I, J, K, and G was conducted.

Over 200 analogs of the aminoacetamide sulfonamide series (confirmed hits I and J) were surveyed by reviewing the screening results from earlier experiments for related structures and by purchasing and assaying additional compounds. The results for a few key analogs, four active and one inactive, are shown in Table 6 along with the screening hit, compound J.

TABLE 6

Preliminary SAR of aminoacetamide sulfonamide scaffold

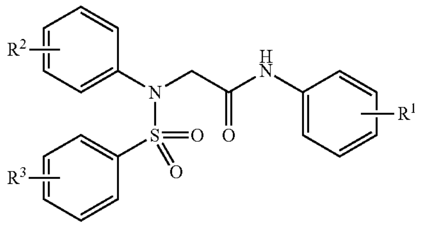

| Cpd | $R^1$ | $R^2$ | $R^3$ | HIV/EBOV GP $IC_{90}$ (μM) | HIV/EBOV GP $CC_{50}$ (μM) | SI |
|---|---|---|---|---|---|---|
| J | 2-Ph | 4-Me | 4-OMe | 0.8 | 80 | 100 |
| 6175342 | 4-OMe | 3-OMe | 4-Me | >100 | >100 | na |
| 6367388 | 2,5-diOMe | 2-Cl | 4-Me | 1.6 | 50 | 31 |
| 6175402 | 3-Me | 2-Cl | 4-Me | 3.2 | >100 | >31 |
| 5534655 | 4-OEt | 4-Me | H | 0.8 | >100 | >125 |
| 6068478 | 2-F | 3-Me | H | 0.8 | 50 | 63 |

Some general conclusions arose from these data. First, the presence of an aromatic group bearing $R^1$ substituents (see, Table 6) appears important for antiviral activity, and second, an aromatic group is not required on the sulfonyl (bearing $R^3$ substituents in Table 6) for activity since aliphatic groups also were tolerated. Finally, a 3-OMe group as $R^2$ is not well-tolerated while a 3-Me is (cf Cpd #6175342 and Cpd #6068478 in Table 6), suggesting some constraints on that part of the inhibitor.

Several triazole thioether (compound K) analogs were also examined, and representative data are presented in Table 7, below.

TABLE 7

Preliminary SAR of triazole thioether scaffold

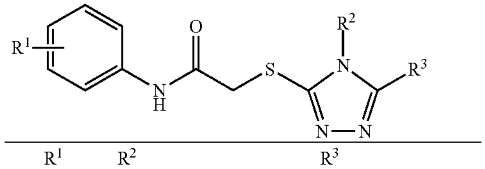

| Cpd | $R^1$ | $R^2$ | $R^3$ | HIV/EBOV GP $IC_{90}$ (μM) | HIV/EBOV GP $CC_{50}$ (μM) | HIV/EBOV GP SI |
|---|---|---|---|---|---|---|
| K | 4-OEt | Ph | 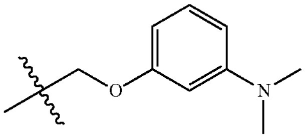 [SMILES: *COc1cccc(N(C)C)c1] | 2.5 | 98 | 39 |
| 7846036 | 3-$CF_3$ | Ph | 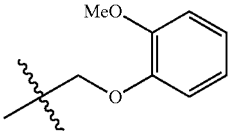 [SMILES: *COc1ccccc1OC] | 6.3 | 55 | 9 |
| 7629169 | 2-Cl | Ph | 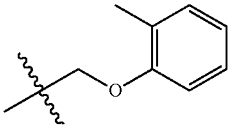 | 2.5 | 21 | 8 |
| 7909196 | 2-$CF_3$ | 4-Tol | 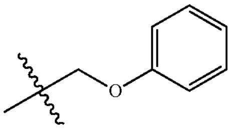 [SMILES: *COc1ccccc1] | 82 | >100 | na |
| 7682333 | 3,4-diMe | Et | 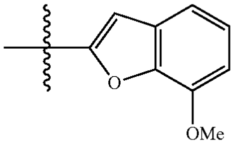 [SMILES: *c1cc2cccc(OC)c2o1] | 6.3 | 35 | 6 |

Preliminary SAR analysis of compound G without altering the benzodiazepine backbone was also performed. Exemplary syntheses of the compounds are described in Example 14, below. As shown in Table 8, a dichloro substitution on the benzene ring of the benzodiazepine core (compound G4) increased activity against the anti-HIV/EBOV-GP pseudotype virus by three fold. In contrast, a bulky phenyl ring (compound G1) or dimethyl substitution (compound G2) decreased the potency. Overall, small substitutions on the diazepine ring of the benzodiazepine are tolerated, while addition of a second aromatic or heteroaromatic group on the azepine ring is detrimental to the antiviral activity. These results suggest that bulky aromatic substitutions on the diazepine ring may introduce some constraints on the inhibitory properties of the compound.

TABLE 8

$IC_{50}$ values for the benzodiazepine analogs

| Compound | Structure | IC50 (μM)[a] |
|---|---|---|
| G | 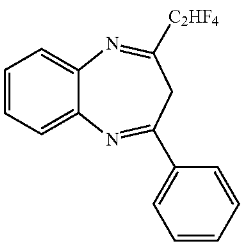 | 12.1 |

TABLE 8-continued
IC50 values for the benzodiazepine analogs
| Compound | Structure | IC50 (μM)[a] |
|---|---|---|
| G1 | 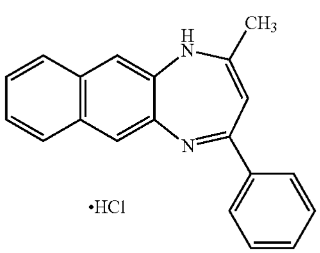 [SMILES: CC1=CC(c2ccccc2)=Nc2cc3ccccc3cc2N1 ; Cl] | 88.3 |
| G2 | 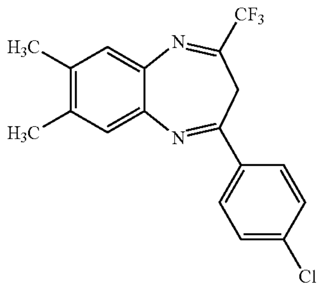 [SMILES: Cc1cc2c(cc1C)N=C(C(F)(F)F)CC(c1ccc(Cl)cc1)=N2] | 72.1 |
| G3 | 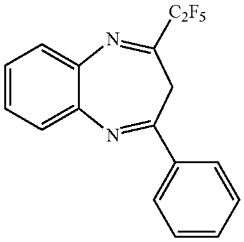 | 70.9 |
| G4 | 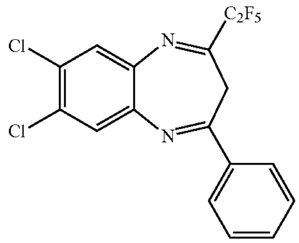 | 3.7 |
| G5 | 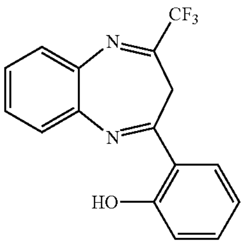 [SMILES: Oc1ccccc1C1=Nc2ccccc2N=C(C(F)(F)F)C1] | 70.7 |
| G6 | 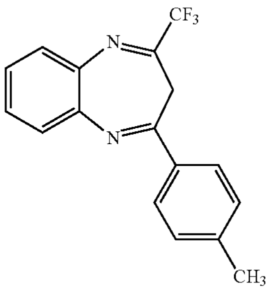 [SMILES: Cc1ccc(C2=Nc3ccccc3N=C(C(F)(F)F)C2)cc1] | 75.7 |
| G7 | 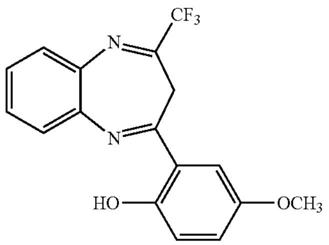 [SMILES: COc1ccc(O)c(C2=Nc3ccccc3N=C(C(F)(F)F)C2)c1] | 85.7 |
| G8 | 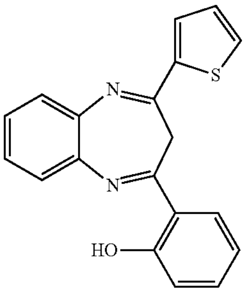 [SMILES: Oc1ccccc1C1=Nc2ccccc2N=C(c2cccs2)C1] | >100 |
| G9 | 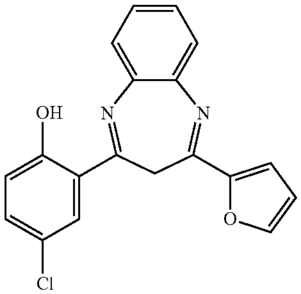 [SMILES: Oc1ccc(Cl)cc1C1=Nc2ccccc2N=C(c2ccco2)C1] | >100 |
| G10 | 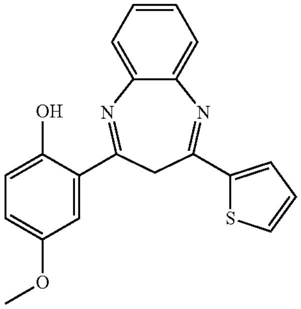 [SMILES: COc1ccc(O)c(C2=Nc3ccccc3N=C(c3cccs3)C2)c1] | >100 |

TABLE 8-continued $IC_{50}$ values for the benzodiazepine analogs

| Compound | Structure | IC50 (μM)[a] |
|---|---|---|
| G11 | 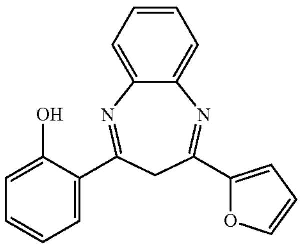 [SMILES: Oc1ccccc1C1=Nc2ccccc2N=C(c2ccco2)C1] | >100 |
| G12 | 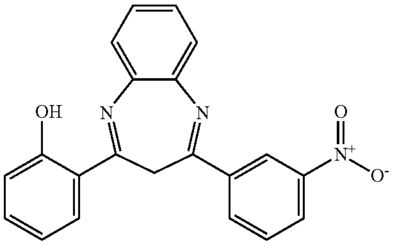 [SMILES: O=[N+]([O-])c1cccc(C2=Nc3ccccc3N=C(c3ccccc3O)C2)c1] | >100 |

[a]HIV/EBOV-GP was generated by transfection of 293T cells with pNL4.3.Luc.R—E— as the HIV-1 expression vector and with EBOV-GP.

[b]293T cells were treated with compound alone. $CC_{50}$ values were determined from linear portions of the dose response curve..

EXAMPLE 14

Syntheses of Additional EBOV Entry Inhibitor Compounds

The following individual compounds were synthesized according the synthesis schemes disclosed, supra:

4,4,5,5-tetrafluoro-1-phenylpentane-1,3-dione, lithium enolate salt (Scheme 1, formula 3; X═H)

A solution of lithium hexamethyldisilazide in THF (1.0 M, 30.2 mL, 30.2 mmol, 1.05 eq.) was added to dry $Et_2O$ (90 mL) and cooled to −78° C. To the cooled solution was added a solution of acetophenone (3.48 g, 28.7 mmol) in $Et_2O$ (8 mL), dropwise over 35 minutes. The mixture was stirred at −78° C. for 20 minutes, then a solution of ethyl 2,2,3,3-tetrafluoropropionate (5.00 g, 28.7 mmol, 1.0 eq.) in $Et_2O$ (8 mL) was added in one portion. The dry ice bath was removed, and the reaction was stirred, warming to room temperature, for 4 hours. The reaction was then evaporated to yield a pink tacky solid which was triturated with hexane repeatedly to yield 6.90 g (95%) of 3 as a pink solid: $R_f$ 0.38 (50% EtOA/hexanes): $^1H$ NMR (DMSO-$d_6$) δ 7.85 (d, 2H), 7.52-7.40 (m, 3H), 6.66 (tt, 1H), 6.18 (s, 1H).

4,4,5,5,5-pentafluoro-1-phenylpentane-1,3-dione, lithium enolate salt (Scheme 1, formula 3; X═F)

A solution of lithium hexamethyldisilazide in THF (1.0 M, 7.6 mL, 7.6 mmol, 1.0 eq.) was added to dry $Et_2O$ (12 mL) and cooled to −78° C. To the cooled solution was added a solution of acetophenone (0.90 g, 7.6 mmol) in $Et_2O$ (8 mL), dropwise over 15 minutes. The mixture was stirred at −78° C. for 30 minutes, then a solution of ethyl 2,2,3,3-3-pentafluoropropionate (1.26 mL, 7.95 mmol, 1.05 eq.) in $Et_2O$ (6 mL) was added in one portion. The dry ice bath was removed, and the reaction was stirred, warming to room temperature, for 1 hour. The reaction was then evaporated to yield a tacky solid which was triturated with hexane repeatedly to yield 2.04 g (99%) of 3 as a pink solid: $R_f$ 0.38 (50% EtOA/hexanes): $^1H$ NMR (DMSO-$d_6$) S 7.96 (d, 2H), 7.64 (t, 1H), 7.52 (dt, 2H), 6.64 (s, 1H).

4-methyl-2-phenylbenzo[b][1,4]diazepine (Scheme 2, formula 6; R═H, R'=Me; HCl salt)

To a solution of AcOH in EtOH (10% v/v; 1.4 mL) were added o-phenyldiamine (0.22 g, 2.0 mmol) and 1-phenylbutane-1,3-dione (0.32 g, 2.0 mmol, 1.0 eq.). The resulting purple solution was heated for 4 minutes at 40° C. (oil bath), then cooled to room temperature. Concentrated aq. HCl (0.6 mL) was added, and the mixture was refrigerated 18 hours. The purple precipitate was collected by filtration, washed with $Et_2O$, and dried to yield 0.41 g (75%) of 6 as a purple solid: mp 207-209° C.; MS (ESI) m/z 235.2 $[M+H]^+$; $^1H$ NMR (DMSO-$d_6$) δ 11.09 (s, 1H), 9.74 (s, 1H), 7.78-7.50 (m, 5H), 7.04-6.94 (m, 4H), 4.62 (s, 1H), 2.04 (s, 3H).

4-methyl-2-phenylnaphtho[2,3-b][1,4]diazepine (Scheme 2, formula 6; R=benzo, R'=Me; HCl salt)

To a solution of AcOH in EtOH (10% v/v; 0.7 mL) were added 2,3-diaminonaphthalene (84 mg, 0.53 mmol) and 1-phenylbutane-1,3-dione (86 mg 0.53 mmol, 1.0 eq.). The resulting purple solution was heated for 60 minutes at 40° C. (oil bath), then cooled to room temperature. Concentrated aq. HCl (0.6 mL) was added, and the mixture was refrigerated 18 hours. The pale blue precipitate was collected by filtration, washed with $Et_2O$, and dried to yield 104 mg (61%) of 6 as a blue-gray solid: mp 178-180° C.; MS (ESI) m/z 285.0 $[M+H]^+$; $^1H$ NMR (DMSO-$d_6$) δ 11.01 (s, 1H), 10.15 (s, 1H), 7.69-7.24 (m, 11H), 4.73 (s, 1H), 2.09 (s, 3H).

4-(1,1,2,2,2-pentafluoroethyl)-2-phenylbenzo[b][1,4]diazepine (Scheme 2, formula 6; R═H, R'═$CF_2CF_3$)

To a suspension of the lithium salt of 4,4,5,5,5-pentafluoro-1-phenylpentane-1,3-dione (0.25 g, 0.92 mmol) in absolute EtOH (7.5 mL) was added a solution of HCl in $Et_2O$ (2.0 M, 0.45 mL, 0.90 mmol). To the resulting mixture was added 1,2-phenyldiamine (80 mg, 0.74 mmol, 0.8 eq) and glacial AcOH (0.46 mL). The resulting red solution was stirred at room temperature for 3 d. The solvent was then removed under vacuum, and the remaining residue was subjected to chromatography on silica gel with 10-20% $CHCl_3$/hexane. Product-containing fractions were pooled and evaporated to yield 120 mg (39%) of 6 as a slightly yellow powder: mp 69-72° C.; MS (ESI) m/z 339.2 $[M+H]^+$; $^1H$ NMR (DMSO-$d_6$) δ 8.09-8.06 (m, 2H), 7.98-7.35 (m, 7H), 3.52 (s, br, 2H).

7,8-dichloro-4-(1,1,2,2,2-pentafluoroethyl)-2-phenylbenzo[b][1,4]diazepine (Scheme 2, formula 6; R═Cl, R'═$CF_2CF_3$)

To a suspension of the lithium salt of 4,4,5,5,5-pentafluoro-1-phenylpentane-1,3-dione (0.25 g, 0.92 mmol) in absolute EtOH (7.5 mL) was added a solution of HCl in $Et_2O$ (2.0 M, 0.45 mL, 0.90 mmol). To the resulting mixture was added 4,5-dichloro-1,2-phenyldiamine (130 mg, 0.74 mmol, 0.8 eq) and glacial AcOH (0.46 mL). The resulting red solution was stirred at room temperature for 3 days. The solvent was then removed under vacuum, and the remaining residue was subjected to chromatography on silica gel with 10-20% $CHCl_3$/hexane. Product-containing fractions were pooled and evaporated to yield 129 mg (35%) of 6 as a slightly yellow powder: mp 131-133° C.; MS (ESI) m/z 407.1 $[M+H]^+$; $^1H$ NMR (DMSO-$d_6$) δ 8.09-8.06 (m, 2H), 7.98-7.35 (m, 7H), 3.52 (s, br, 2H).

4-(1,1,2,2-tetrafluoroethyl)-2-phenylbenzo[b][1,4]diazepine (Scheme 2, formula 6; R=H, R'=$CF_2CHF_2$)

To a suspension of the lithium salt of 4,4,5,5-tetrafluoro-1-phenylpentane-1,3-dione (0.40 g, 1.6 mmol) in absolute EtOH (12 mL) was added a solution of aq. HCl (3.0 M, 0.53 mL, 1.5 mmol). To the resulting mixture was added 1,2-phenyldiamine (136 mg, 1.3 mmol, 0.8 eq) and glacial AcOH (1.1 mL). The resulting solution was stirred at room temperature for 12 hours. The reaction was diluted with $CHCl_3$ (100 mL), washed with water (50 mL×4), dried over $Na_2SO_4$, filtered, and evaporated. The remaining residue was subjected to chromatography on silica gel with 10-20% $CHCl_3$/hexane. Product-containing fractions were pooled and evaporated to yield 112 mg (46%) of 6 as an off-white powder: mp 83-85° C.; $^1H$ NMR (DMSO-$d_6$) δ 8.12-8.08 (m, 2H), 7.60-7.26 (m, 7H), 6.38 (tt, 1H), 3.51 (s, br, 2H).

7.8-dichloro-4-(1,1,2,2-tetrafluoroethyl)-2-phenylbenzo[b][1,4]diazepine (Scheme 2, formula 6; R=H, R'=$CF_2CHF_2$)

To a suspension of the lithium salt of 4,4,5,5-tetrafluoro-1-phenylpentane-1,3-dione (0.50 g, 1.8 mmol) in absolute EtOH (16 mL) was added a solution of aq. HCl (3.0 M, 0.66 mL, 2.0 mmol). To the resulting mixture was added 4,5-dichloro-1,2-phenyldiamine (278 mg, 1.6 mmol, 0.8 eq) and glacial AcOH (1.4 mL). The resulting solution was stirred at room temperature for 2 days. The solvent was then removed under vacuum, and the remaining residue was subjected to chromatography on silica gel with 10-20% $CHCl_3$/hexane. Product-containing fractions were pooled and evaporated to yield 205 mg (34%) of 6 as a white powder: mp 119-120° C.; $^1H$ NMR (DMSO-$d_6$) δ 8.08 (dd, 2H), 7.70 (s, 1H), 7.65 (s, 1H), 7.56-7.46 (m, 3H), 6.32 (tt, 1H), 3.54 (s, br, 2H).

5,7-dinitro-8-[methyl(propyl)amino]quinoline (Scheme 3, formula 8)

8-Chloro-5,7-dinitroquinoline (301 mg, 1.19 mmol) and N-methyl-1-propylamine (0.30 mL, 2.8 mmol, 2.4 eq) were dissolved in EtOH (4 mL). The mixture was heated to 80° C. (oil bath) for 16 hours. The reaction mixture was then cooled to provide a crystalline solid which was collected by filtration, washed with cold EtOH, and dried to yield 283 mg (82%) of 8 as a dark red crystalline solid: $R_f$ 0.72 (50% EtOAc-Hexanes); mp 92-93° C.; $^1H$ NMR ($CDCl_3$): 9.27 (dd, 1H), 8.95 (s, 1H), 8.93 (dd, 1H), 7.68 (dd, 1H), 3.77 (t, 2H), 3.25 (s, 3H), 1.85 (sextet, 2H), 0.93 (t, 3H).

2-methyl-3-phenyl-3H-quinazolin-4-one (Scheme 4, formula 14; R=H)

A mixture of 2-methyl-4H-Benzo[d][1,3]oxazin-4-one (12; 1.0 g, 6.2 mmol) and aniline (13, R=H, 0.57 mL, 6.2 mmol, 1.0 eq) were heated at 160° C. (oil bath) for 12 hours. The reaction was cooled to room temperature and the resulting solid was recrystallized from EtOH to yield 485 mg (31%) of 14 as a yellow-orange crystalline solid: $^1H$ NMR ($CDCl_3$): 8.28 (d, 1H), 7.80-7.67 (m, 2H), 7.60-7.44 (m, 4H), 7.29-7.28 (m, 2H), 2.25 (s, 3H).

2-methyl-3-(3-trifluoromethylphenyl)-3H-quinazolin-4-one (Scheme 4, formula 14; R=$CF_3$)

A mixture of 2-methyl-4H-Benzo[d][1,3]oxazin-4-one (12; 1.0 g, 6.2 mmol) and 3-trifluoromethylaniline (13, R=H, 0.77 mL, 6.2 mmol, 1.0 eq) were heated at 160° C. (oil bath) for 12 hours. The reaction was cooled to room temperature and the resulting solid was subjected to chromatography on silica gel with 20-50% EtOAc/hexane. Product-containing fractions were pooled and evaporated to yield 1.08 g mg (56%) of 14 as a yellow solid: $^1H$ NMR ($CDCl_3$): 8.27 (d, 1H), 7.29-7.28 (m, 7H), 2.25 (s, 3H).

2-[2-(5-nitrofuran-2-yl)vinyl]-3-phenyl-3H-quinazolin-4-one (Scheme 4, formula 16; R=H, R'=$NO_2$)

A mixture of 2-methyl-3-phenyl-3H-quinazolin-4-one (14; R=H; 150 mg, 0.64 mmol), 5-nitro-furan-2-carbaldehyde (15, R=$NO_2$; 90 mg, 0.64 mmol, 1.0 eq) and sodium acetate (5 mg; 0.04 mmol, 6 mol %) in AcOH (0.65 mL) were heated to reflux for 1.5 hours. The mixture was then cooled to room temperature and hexane was added until a precipitate formed. The resulting solid was collected by filtration and dried to yield 129 mg (56%) of 16 as a brown powder: $R_f$ 0.48 (50% EtOAc/hexanes); mp>240° C. (dec.); MS (ESI) m/z 360.2 $[M+H]^+$; $^1H$ NMR ($CDCl_3$) 8.33-8.30 (d, 1H), 7.85-7.49, (m, 10H), 6.66-6.57 (m, 2H).

2-[2-(5-chlorofuran-2-yl)vinyl]-3-phenyl-3H-quinazolin-4-one (Scheme 4, formula 16; R=H, R'=Cl)

A mixture of 2-methyl-3-phenyl-3H-quinazolin-4-one (14; R=H; 140 mg, 0.59 mmol), 5-nitro-furan-2-carbaldehyde (15, R=Cl; 77 mg, 0.59 mmol, 1.0 eq) and sodium acetate (5 mg; 0.04 mmol, 7 mol %) in AcOH (0.65 mL) were heated to reflux for 1.5 hours. The mixture was then cooled to room temperature and hexane was added until a precipitate formed. The resulting solid was collected by filtration and dried to yield 141 mg (68%) of 16 as a brown powder: $R_f$ 0.60 (50% EtOAc/hexanes); mp>240° C. (dec.); MS (ESI) m/z 349.1 $[M+H]^+$; $^1H$ NMR ($CDCl_3$) 8.30-8.27 (d, 1H), 7.75-7.26 (m, 10H), 6.506 (s, 1H), 6.25-6.20 (m, 2H).

2-[2-(furan-2-yl)vinyl]-3-(3-trifluoromethyl)phenyl-3H-quinazolin-4-one (Scheme 4, formula 16; R=$CF_3$, R'=H)

A mixture of 2-methyl-3-phenyl-3H-quinazolin-4-one (14; R=$CF_3$; 104 mg, 0.34 mmol), furan-2-carbaldehyde (15, R=H, 0.05 mL, 0.63 mmol, 2 eq) and sodium acetate (5 mg; 0.04 mmol, 12 mol %) in AcOH (0.65 mL) were heated to reflux for 1.5 hours. The mixture was then cooled to room temperature and hexane was added until a precipitate formed. The resulting solid was collected by filtration and dried to yield 127 mg (52%) of 16 as a tan powder: $R_f$ 0.48 (50% EtOAc/hexanes); mp 197-199° C.; MS (ESI) m/z 383.3 $[M+H]^+$; $^1H$ NMR ($CDCl_3$) 8.29 (d, 1H), 7.77-7.36 (m, 9H), 6.57 (s, 1H), 6.42 (s, 1H), 6.18 (d, 1H).

2-[2-(5-nitrofuran-2-yl)vinyl]-3-(3-trifluoromethylphenyl)-3H-quinazolin-4-one (Scheme 4, formula 16; R═$CF_3$, R'═$NO_2$)

A mixture of 2-methyl-3-(3-trifluoromethylphenyl)-3H-quinazolin-4-one (14; R═$CF_3$; 194 mg, 0.64 mmol), 5-nitrofuran-2-carbaldehyde (15, R═$NO_2$; 90 mg, 0.64 mmol, 1.0 eq) and sodium acetate (5 mg; 0.04 mmol, 6 mol %) in AcOH (0.65 mL) were heated to reflux for 1.5 hours. The mixture was then cooled to room temperature and hexane was added until a precipitate formed. The resulting solid was collected by filtration and dried to yield 166 mg (61%) of 16 as an orange powder: $R_f$ 0.50 (50% EtOAc/hexanes); mp 228-230° C.; MS (ESI) m/z 428.2 $[M+H]^+$; $^1H$ NMR ($CDCl_3$) 8.16-7.50 (m, 10H), 7.20 (s, 1H), 6.40-6.34 (d, 1H).

2-[2-(5-chlorofuran-2-yl)vinyl]-3-(3-trifluoromethylphenyl)-3H-quinazolin-4-one (Scheme 4, formula 16; R═$CF_3$, R'═Cl)

A mixture of 2-methyl-3-(3-trifluoromethylphenyl)-3H-quinazolin-4-one (14; R═$CF_3$; 194 mg, 0.64 mmol), 5-chlorofuran-2-carbaldehyde (15, R═Cl; 83 mg, 0.64 mmol, 1.0 eq) and sodium acetate (5 mg; 0.04 mmol, 6 mol %) in AcOH (0.65 mL) were heated to reflux for 1.5 hours. The mixture was then cooled to room temperature and hexane was added until a precipitate formed. The resulting solid was collected by filtration and dried to yield 115 mg (43%) of 16 as a tan powder: $R_f$ 0.68 (50% EtOAc/hexanes); mp 191-193° C.; MS (ESI) m/z 417.0 $[M+H]^+$; $^1H$ NMR ($CDCl_3$) 8.28 (d, 1H), 7.82-7.48 (m, 8H), 6.54 (s, 1H), 6.21-6.11 (m, 2H).

All publications, patent applications, patents, and other documents cited herein are incorporated by reference in their entirety. Obvious variations to the disclosed compounds and alternative embodiments of the invention will be apparent to those skilled in the art in view of the foregoing disclosure. All such obvious variants and alternatives are considered to be within the scope of the invention as described herein.

We claim:

1. A method for treating an individual infected with or exposed to a filovirus comprising administering to said individual, as an active ingredient, a compound of the formula J-1:

J-1

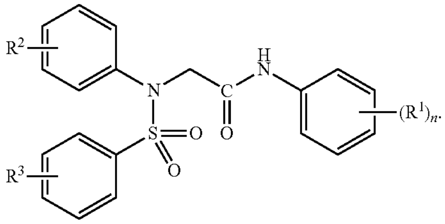

wherein n is 0, 1, or 2;

$R^1$ is at the meta-, ortho-, or para- position and is independently selected from $C_{1-2}$ alkyl, $C_{1-2}$ alkoxy, chloro, fluoro, and phenyl;

$R^2$ is at the meta-, ortho-, or para- position and is selected from hydrogen, $C_{1-2}$ alkyl, $C_{1-2}$ alkoxy, chloro, and fluoro; and $R^3$ is at the meta-, ortho-, or para- position and is selected from hydrogen, $C_{1-2}$ alkyl, and $C_{1-2}$ alkoxy.

2. The method according to claim 1, wherein said individual is human.

3. The method according to claim 1, wherein said filovirus is Marburg virus or Ebola virus.

4. The method according to claim 3, wherein said filovirus is Ebola virus.

5. The method according to claim 4, wherein said Ebola virus is a strain selected from the Ivory Coast, Sudan, Zaire, Bundibugyo and Reston species.

6. The method according to claims 1, further comprising administering an additional active ingredient in conjunction with said filovirus entry inhibitor compound, said additional active ingredient being selected from the group consisting of an antibiotic, an antibody, an antiviral agent, an anticancer agent, an analgesic, an immunostimulatory agent, a natural, synthetic or semi-synthetic hormone, a central nervous system stimulant, an antiemetic agent, an anti-histamine, an erythropoietin, a complement stimulating agent, a sedative, a muscle relaxant agent, an anesthetic agent, an anticonvulsive agent, an antidepressant, an antipsychotic agent, and combinations thereof.

* * * * *